United States Patent
Mantell et al.

(10) Patent No.: US 10,661,034 B2
(45) Date of Patent: May 26, 2020

(54) HIGH RESOLUTION SYSTEM AND METHOD FOR CONTROLLING HIGH AND LOW INSUFFLATION FLOW RATES

(71) Applicant: Northgate Technologies Inc., Elgin, IL (US)

(72) Inventors: Robert R. Mantell, Arlington Heights, IL (US); Eric Andersen, Palatine, IL (US); Steven Weaver, Itasca, IL (US); Paul Wilk, Schaumburg, IL (US)

(73) Assignee: Northgate Technologies Inc., Elgin, IL (US)

( * ) Notice: Subject to any disclaimer, the term of this patent is extended or adjusted under 35 U.S.C. 154(b) by 471 days.

(21) Appl. No.: 15/503,755

(22) PCT Filed: Aug. 14, 2015

(86) PCT No.: PCT/IB2015/056209
§ 371 (c)(1),
(2) Date: Feb. 14, 2017

(87) PCT Pub. No.: WO2016/024253
PCT Pub. Date: Feb. 18, 2016

(65) Prior Publication Data
US 2017/0274160 A1    Sep. 28, 2017

Related U.S. Application Data

(60) Provisional application No. 62/037,893, filed on Aug. 15, 2014.

(51) Int. Cl.
*A61M 13/00* (2006.01)
*A61M 39/24* (2006.01)
(Continued)

(52) U.S. Cl.
CPC .......... *A61M 13/003* (2013.01); *A61M 39/24* (2013.01); *A61M 2205/15* (2013.01);
(Continued)

(58) Field of Classification Search
CPC ... A61M 13/003; A61M 39/24; A61M 16/024
See application file for complete search history.

(56) References Cited

U.S. PATENT DOCUMENTS

| 5,292,304 A | 3/1994 | Mantell et al. |
| 5,328,458 A * | 7/1994 | Sekino ................ A61M 13/003 604/23 |

(Continued)

FOREIGN PATENT DOCUMENTS

| CN | 101897605 A | 12/2010 |
| CN | 202057361 U | 11/2011 |

(Continued)

OTHER PUBLICATIONS

Chinese Office Action and Search Report dated Jun. 25, 2019 for corresponding Chinese Application No. 201580055027.3 including translation.
(Continued)

*Primary Examiner* — Bhisma Mehta
*Assistant Examiner* — Nidah M Hussain
(74) *Attorney, Agent, or Firm* — Brinks Gilson & Lione

(57) ABSTRACT

Insufflation systems including a plurality of flow rate sensors are disclosed. Each flow rate sensor is configured to measure flow across a different flow rate range, with the combined flow rate ranges of the sensors encompassing the entire flow rate capability of the insufflation system. A controller selects the most appropriate flow rate sensor based on the gas flow required to be delivered to the patient.

24 Claims, 11 Drawing Sheets

(52) U.S. Cl.
CPC .............. *A61M 2205/3334* (2013.01); *A61M 2205/3344* (2013.01); *A61M 2205/3561* (2013.01); *A61M 2205/3584* (2013.01); *A61M 2205/50* (2013.01); *A61M 2205/505* (2013.01); *A61M 2205/52* (2013.01); *A61M 2205/7545* (2013.01); *A61M 2210/1021* (2013.01)

(56) References Cited

U.S. PATENT DOCUMENTS

| | | | | |
|---|---|---|---|---|
| 5,476,447 | A | * | 12/1995 | Noda ................. A61B 18/1482 604/26 |
| 5,800,381 | A | | 9/1998 | Ognier |
| 6,299,592 | B1 | * | 10/2001 | Zander ................ A61M 13/003 600/560 |
| 7,988,656 | B2 | | 8/2011 | Uesugi et al. |
| 2005/0081541 | A1 | * | 4/2005 | Copping ................ A61B 18/02 62/177 |
| 2013/0118486 | A1 | * | 5/2013 | Schnitman ........ A61M 16/0051 128/202.22 |
| 2015/0233879 | A1 | * | 8/2015 | Tolmie ................ A61M 16/201 128/202.22 |

FOREIGN PATENT DOCUMENTS

| | | |
|---|---|---|
| CN | 202109938 U | 1/2012 |
| JP | 1993-329098 | 12/1993 |
| JP | 2665110 B2 | 10/1997 |
| JP | 2011-518617 | 6/2011 |
| WO | WO 2005/117779 A1 | 12/2005 |
| WO | WO 2009/132127 A1 | 10/2009 |

OTHER PUBLICATIONS

Translation of Japanese Office Action dated May 28, 2019 for corresponding Japanese Application No. 2017-527987.
International Search Report dated Jan. 5, 2016 in International Application No. PCT/IB2015/056209, 2 pages.
Written Opinion of the International Search Authority dated Jan. 5, 2016 in International Application No. PCT/IB2015/056209, 5 pages.
PCT Recordation of Search History dated Jan. 5, 2016, in International Application No. PCT/IB2015/056209, 3 pages.
Translation of Japanese Office Action and Supplemental Search Report for counterpart JP 201580055027.3 dated Mar. 10, 2020 (13 pages).
Examination Report from counterpart Australian Patent Application No. 2015302928 dated Mar. 26, 2020 (4 pages).

* cited by examiner

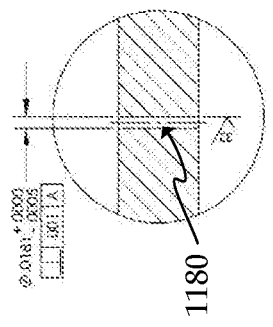
FIG. 11F
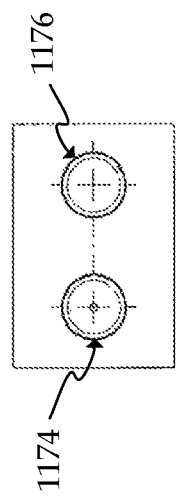
FIG. 11E
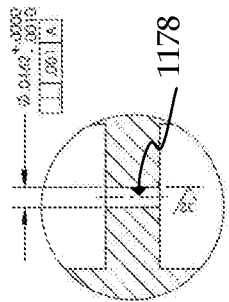
FIG. 11C
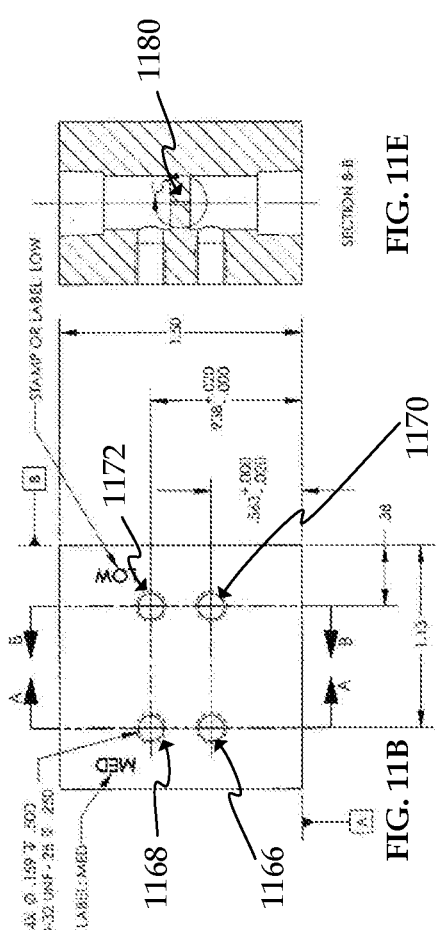
FIG. 11B
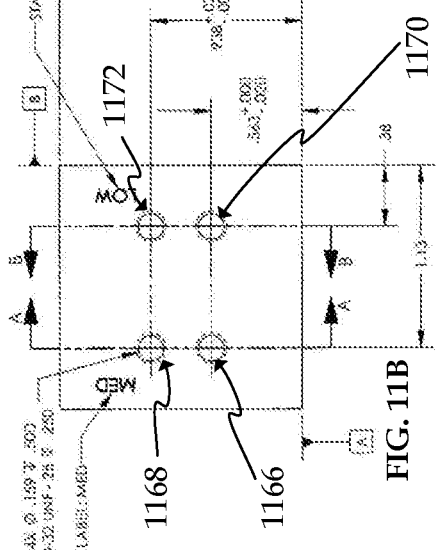
FIG. 11D
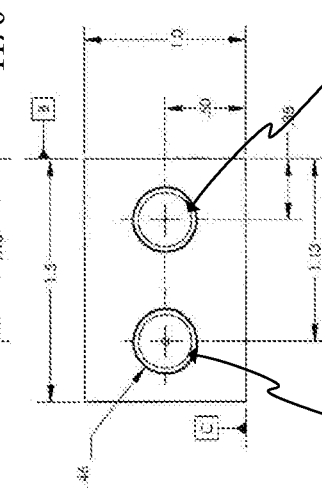
FIG. 11H
FIG. 11G
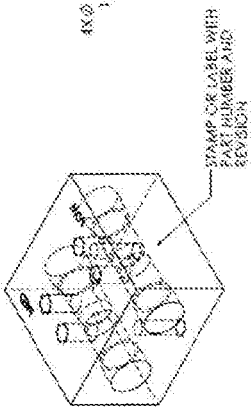
FIG. 11A

HIGH RESOLUTION SYSTEM AND METHOD FOR CONTROLLING HIGH AND LOW INSUFFLATION FLOW RATES

BACKGROUND

1. Technical Field

The present disclosure relates to insufflators used in minimally invasive surgery, and in particular, the control and measurement of gas flow in insufflators.

2. Background Information

Gas insufflators have been used in the medical field for more than 30 years, primarily during minimally invasive surgery, such as laparoscopic surgery. Insufflators provide work-space for surgeons to operate within a patient's abdominal (peritoneal) cavity. The required work-space is created by delivering gas that inflates the abdominal cavity. Inflating the abdominal cavity with gas achieves what is known as pneumoperitoneum. The performance and functionality of insufflators has been evolving as more and more demands have been placed on insufflators due to increase in laparoscopic surgeries. Insufflators are now used in simple laparoscopic surgeries, such as cholecystectomy, hernia operation, and appendectomy, as well as complex laparoscopic surgeries, such as gastric bypass, lap band operations, and hysterectomy. Consequently, insufflators have had to increase their flow rates, while still maintaining acceptable pressure and flow measurement control and accuracy. The maximum flow rate capability of insufflators has increased from 9 liters per minute to 50 liters per minute and more in order to keep up with the ever increasing demands of maintaining proper pneumoperitoneum. Recently, insufflators have included pre-programmed performance ranges to account for the special needs of various surgeries, such as minimally invasive pediatric laparoscopic surgery. Pediatric laparoscopic surgery requires very low flow rates with very high accuracy and very tight range of control due to the relatively small size of the patients. Flow rates as low as 0.1 liters per minute must be controlled with accuracy tight range of control, such as plus or minus 0.03 liters per minute. There is a need for an insufflation system, apparatus, and method that meets the flow rate demands of laparoscopic surgery with acceptable accuracy and range of control to ensure patient safety.

BRIEF SUMMARY

In one aspect, an insufflation system that is configured for surgical use with a patient includes a plurality of flow rate sensors, where each of the flow rate sensors is configured to measure flow across a different flow rate range. A first valve is in fluid communication with the plurality of flow rate sensors and a primary gas delivery line that is connectable to the patient. A controller is configured to select one of the plurality of flow rate sensors based on a desired flow through the first valve.

In another aspect, a method of operating an insufflation system configured for surgical use with a patient, where the system has a plurality of flow rate sensors in fluid communication with a first valve and each of the flow rate sensors is configured to measure flow across a different flow rate range, the method performed in a controller in communication with the first valve and the plurality of flow rate sensors includes the steps of determining which of the plurality of flow rate sensors is to be selected; determining a desired flow rate through the first valve based on a desired pressure in a patient's abdominal cavity and a current pressure detected in a patient's abdominal cavity; selecting a flow rate sensor different than the currently selected flow rate sensor if the desired flow rate through the first valve is outside of a flow rate range of the currently selected flow rate sensor; measuring flow through the first valve with the selected flow rate sensor; and regulating the first valve to control the flow rate through the first valve.

Other systems, methods, features and advantages will be, or will become, apparent to one with skill in the art upon examination of the following figures and detailed description. It is intended that all such additional systems, methods, features and advantages be included within this description, be within the scope of the invention, and be protected by the following claims.

BRIEF DESCRIPTION OF THE DRAWINGS

FIG. 11 includes perspective, planar, and cross-sectional views of a manifold according to an embodiment.

FIG. 12 is a block diagram of an insufflation system according to an embodiment.

FIG. 13 is a block diagram of an insufflation system according to an embodiment.

FIG. 14 is a block diagram of an insufflation system according to an embodiment.

FIG. 15 is a block diagram of an insufflation system according to an embodiment.

FIG. 16 is a block diagram of an insufflation system according to an embodiment.

FIG. 17 is a block diagram of an insufflation system according to an embodiment.

FIG. 18 is graphs of the resolution of a flow rate sensor of an insufflation system according to an embodiment.

FIG. 19 is graphs of the resolution of a flow rate sensor of an insufflation system according to an embodiment.

FIG. 20 is graphs of the resolution of a flow rate sensor of an insufflation system according to an embodiment.

FIG. 21 is graphs of the resolution of a flow rate sensor of an insufflation system according to an embodiment.

FIG. 22 is graphs of the resolution of a flow rate sensor of an insufflation system according to an embodiment.

DETAILED DESCRIPTION

The present disclosure is directed to a system and method for controlling the flow rate of insufflation gas from an insufflator to a patient.

The present disclosure provides a cost effective, highly efficient insufflation system that can provide high flow rate and pressure accuracy at both high and low flow rates. The insufflation systems utilize components and algorithms that allow a control system to select the proper measurement components as the insufflation system transitions from low to high flow rates, and vice-versa.

Figure 1:
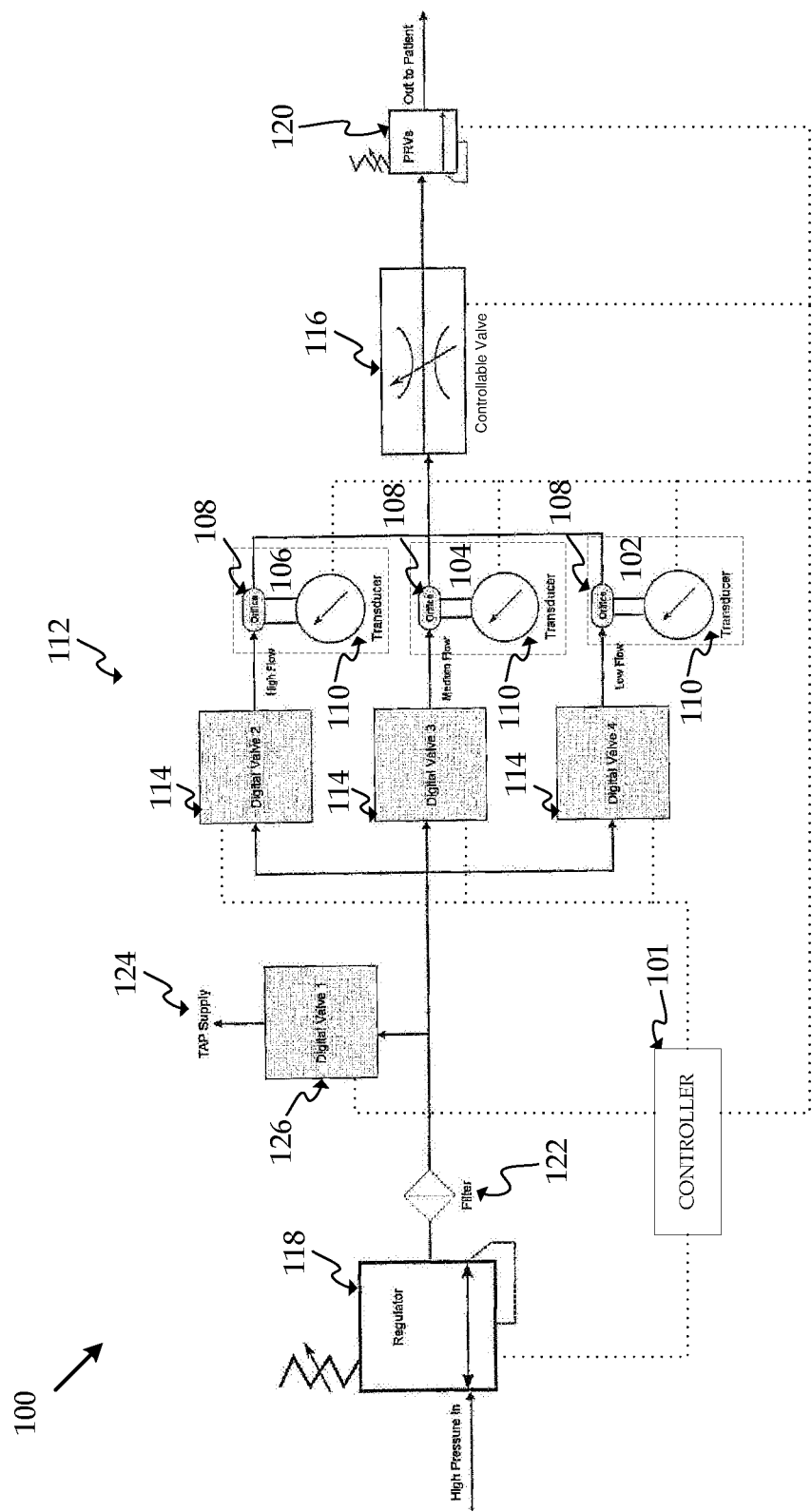
FIG. 1 is a block diagram of an insufflation system according to an embodiment.

Referring to FIG. 1, an embodiment of an insufflation system 100 is shown. The controller unit 101 in insufflation system 100 varies the flow of gas to a patient's abdominal cavity in order to pressurize the abdominal cavity. An abdominal cavity pressurized with gas is referred to as pneumoperitoneum. Pneumoperitoneum raises the abdominal wall from the organs and creates a viewing and operating space within the patient's abdominal cavity for a surgeon. Pressure in the abdominal cavity may vary during an operation, such as when equipment is removed or when pressure is applied to the outside of the abdominal cavity. Maintaining stable pressure within the abdominal cavity is important for patient safety. It is critical for patient safety not to overpressurize the patient, especially pediatric patients who are more sensitive to injury than adult patients. High accuracy pressure control is critical and, therefore, high accuracy gas flow rate measurement is critical because abdominal pressure is controlled with gas flow to the abdomen. The acceptable level of accuracy, when measured as a percentage, may vary depending on the flow rate. Lower percent accuracy may be acceptable at relatively low flow rates, whereas higher percent accuracy may be acceptable at relatively high flow rates. For example, an accuracy of plus or minus 30% may be acceptable at flow rates near or below 1 liter per minute, whereas an accuracy of plus or minus 5% may be acceptable at flow rates near or above 10 liters per minute. Low accuracy flow rate measurement may cause the insufflation system to deliver more gas to the patient than was requested by the controller unit 101, which may overpressurize the abdominal cavity and is an inefficient use of insufflation gas. Low accuracy flow rate measurement may also cause the insufflation system to delivery less gas to the patient than was requested by the controller unit 101, which may delay achieving pneumoperitoneum and may impede the surgeon or extend the operation. High accuracy flow rate measurement may allow the insufflation system to deliver the optimum gas flow to the patient. The optimum gas flow is the maximum flow that can be delivered by the insufflation system with any downstream restrictions, such as tubing, needles, and trocars, without exceeding the desired pressure level in the patient's abdominal cavity. High accuracy flow rate measurement is especially important for operations with pediatric patients because the cumulative flow of gas to reach pneumoperitoneum is much less than with adult patients due to the relatively small size of pediatric abdominal cavities. For example, pediatric applications may require gas flow rates as low as 0.1 liters per minute up to 5 liters per minute, whereas adult applications may utilize gas flow rates as high as 50 liters per minute or more.

The insufflation system 100 includes flow rate sensors 102, 104, and 106. As is known in the art, flow rate sensors 102, 104, and 106 may measure the flow rate of a gas by measuring the pressure of the gas upstream and downstream of a known pressure drop region, such as an orifice, and calculating the flow rate based on the measured differential pressure. Alternatively, flow rate sensors 102, 104, and 106 may use any other known means of measuring fluid flow. Flow rate sensors 102, 104, and 106 may each include orifices 108 and pressure measurement transducers 110. Flow rate sensors 102, 104, and 106 may each include one or more redundant pressure measurement transducers.

Flow rate sensors 102, 104, 106 may be designed for specific flow rate ranges, such as for example, low flow, medium flow, and high flow. For example, the low flow rate range may be from 0 liters per minute to approximately 1 liter per minute, the medium flow rate range may be from approximately 1 liter per minute to approximately 8 liters per minute, and the high flow rate range may be from approximately 8 liters per minute to the maximum flow rate of the insufflator, such as 50 liters per minute or more. The number of flow rate ranges and the span of individual flow rate ranges may vary depending on the application of the system. The combined flow rate ranges of all the flow rate sensors may encompass the entire flow rate capability of the insufflation system, such as 0 liters per minute to 50 liters per minute or more. Insufflation system 100 may include more or fewer than three flow rate sensors. The number of flow rate sensors to include may be based on the desired resolution or accuracy of the measured flow rate. Higher accuracy may be achieved by including more flow rate sensors with relatively smaller flow rate ranges for each sensor. The output signals of the flow rate sensors may be fed into an analog to digital converter in order to facilitate processing by controller unit 101. Reducing the flow rate range of each sensor will improve resolution because a smaller flow rate range will be spread across the analog to digital conversion range. If a sensor has 38,000 digital output data points available, every liter per minute will have 760 data points if the flow range is 0 to 50 liters per minute, whereas every liter per minute will have 3,800 data points if the flow range is 0 to 10 liters per minute.

The individual flow rate ranges, such as low, medium, and high, may fully or partially overlap one or more of the adjacent flow rate ranges to create hysteresis. For example, the low flow rate range may extend to 1.1 liters per minute on its upper end, while the medium flow rate range may extend to 0.9 liters per minute on its lower end. Switching from low flow to medium flow may occur at 1.1 liters per minute when the flow is increasing, whereas switching back to low flow from medium flow may occur at 0.9 liters per minute when the flow is decreasing. The overlap of flow rate ranges may allow a control system that switches between flow rate ranges to avoid rapidly oscillating back and forth between two flow rate ranges. The overlap of flow rate ranges may also allow the control system to avoid unnecessary switching between flow rate ranges.

Flow rate sensors 102, 104, and 106 are in fluid communication with manifold 112. Manifold 112 may distribute flow from a single inlet connection to flow rate sensors 102, 104, 106 and out to a single outlet connection. Alternatively, manifold 112 may include multiple inlet and outlet connections. The inlet of manifold 112 may be directly or indirectly connected to a high pressure source of gas that is used with an insufflator, such as carbon dioxide. The outlet of manifold 112 may be directly or indirectly connected to tubing that delivers gas to a patient. Manifold 112 may include one or more assemblies that may be connected through tubing or other fluid communication methods. Manifold 112 may be machined from a block of material, such as aluminum or any other suitable solid material. Manifold 112 may include flow paths specially designed and sized for the gas flow range of each flow rate sensor. Orifices 108 may be included in manifold 112. Orifices 108 may be sized to achieve a pressure drop within the range where the particular flow sensor operates. For example, the orifice for a low flow range sensor may have a diameter of approximately 0.02 inches, the orifice for a medium flow range sensor may have a diameter of approximately 0.05 inches, and the orifice for a high flow range sensor may have a diameter of approximately 0.1 inches. The size of an orifice may be optimized for a particular flow range. Various fluid control equipment, such as tubing, elbows, flanges, and valves may be included or attached to manifold 112 to allow manifold 112 to direct flow to specific flow paths. Additionally or alternatively, fluid control equipment may be located between different assemblies that make up manifold 112, or upstream or downstream of manifold 112. As is understood in the art, various pieces of equipment may or may not be used to connect insufflation system 100 to the patient, such as gas tubing, Verres needles, and trocars.

Insufflation system 100 may include one or more valves 114 to affect the flow of gas through a flow path, such as a flow path to flow rate sensors 102, 104, 106 as shown in FIG. 1. Valves 114 may be on-off valves, variable orifice valves, or any other valve known to influence gas flow. Valves 114 may be electronically monitored and controlled by controller unit 101. The controller unit 101 may adjust valves 114 as necessary to control the flow of gas to flow rate sensors 102, 104, and 106. Valves 114 may be used to direct gas flow to a particular flow rate sensor or sensors and may be used to obstruct gas flow to a particular flow rate sensor or sensors. For example, the valve 114 associated with flow rate sensor 102 may be open and the valves 114 associated with flow rate sensors 104 and 106 may be closed. Accordingly, the gas flow through flow rate sensor 102 will be the same as the gas flow delivered to the patient through controllable valve 116.

In insufflation system 100, controllable valve 116 is located downstream of flow rate sensors 102, 104, 106 and upstream of the gas outlet leading to the patient. Controllable valve 116 works in conjunction with flow rate sensors 102, 104, 106, orifices 108, and the controller unit 101 to allow very precise flow rates using a closed loop system. Flow rate sensors 102, 104, and 106 measure the gas flow being delivered to the patient by way of controllable valve 116. One of skill in the art will recognize that the flow through a valve does not need to be measured directly at the valve, but may be measured upstream or downstream of the valve. Controllable valve 116 may be any type of valve able to control gas flow rates, for example by varying the area and/or pressure drop through the valve. Controllable valve 116 may be adjusted by the controller unit 101 to result in a specific, requested flow to the patient through controllable valve 116.

The controller unit 101 may request a specific flow through controllable valve 116 in order to deliver the specific flow of gas to the patient. The controller unit 101 may request a specific flow to be delivered to the patient in order to achieve a specific pressure in the patient's abdominal cavity. The controller unit 101 may adjust the requested flow based on operating parameters and mode of insufflation system 100, gas pressure in insufflation system 100, type of patient, user input, and/or difference between the measured pressure in the patient's abdominal cavity and the desired pressure in the patient's abdominal cavity. For example, if 15 millimeters of mercury ("mmHg") of pressure is desired in the patient's abdominal cavity and the pressure in the abdominal cavity is currently 5 mmHg the controller unit 101 may request a larger flow than if the pressure in the abdominal cavity is 10 mmHg.

The controller unit 101 may adjust the controllable valve 116 to achieve the requested flow based on any factor in insufflation system 100 that can affect gas flow. For example, the controller unit 101 may adjust controllable valve 116 based on the gas pressure at the inlet to insufflation system 100, the gas pressure downstream of any pressure regulator, the gas pressure at the inlet of controllable valve 116, the gas flow path through manifold 112 including any orifice, any pressure drop upstream of controllable valve 116, and/or any pressure drop downstream of controllable valve 116 such as tubing and equipment connecting the insufflation system to a patient.

Figure 2:
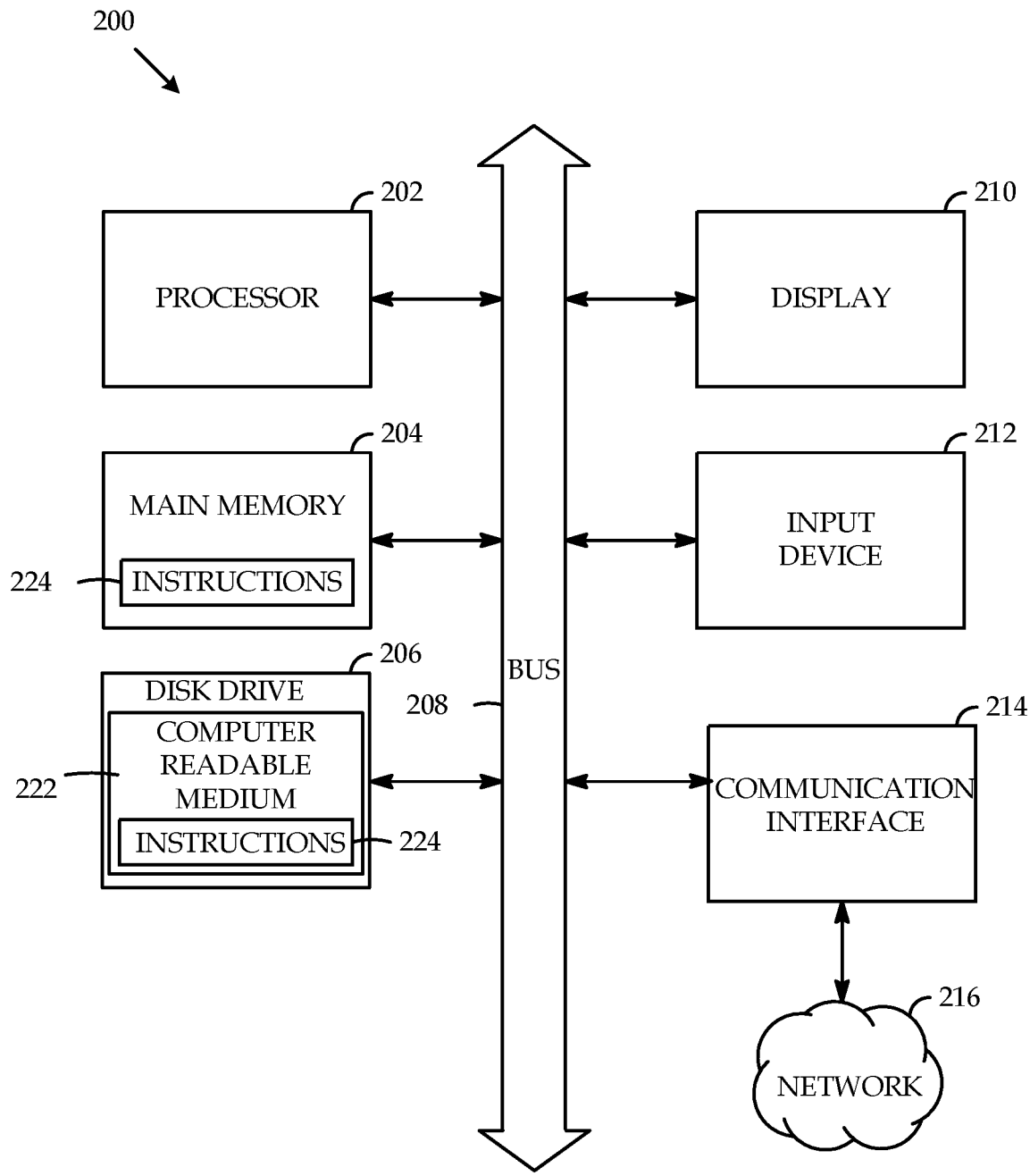
FIG. 2 is an illustrative example of an embodiment of a controller unit.

FIG. 2 is an illustrative example of an embodiment of a controller unit 200 usable with the insufflation system 100 of FIG. 1. For example, controller unit 101 may include one or more of the components and functionality of controller unit 200. The example embodiment of controller unit 200 may be used with the insufflation systems shown in FIGS. 5-9 and described below. The controller unit 200 may include a processor 202, such as, a central processing unit (CPU), a graphics processing unit (GPU), or both. The processor 202 may be one or more general processors, digital signal processors, application specific integrated circuits, field programmable gate arrays, servers, networks, digital circuits, analog circuits, combinations thereof, or other now known or later developed devices for analyzing and processing data. The processor 202 may implement a software program, such as code generated manually (i.e., programmed).

The controller unit 200 may include a memory 204 that can communicate via a bus 208. The memory 204 may be a main memory, a static memory, or a dynamic memory. The memory 204 may include, but may not be limited to computer readable storage media such as various types of volatile and non-volatile storage media, including but not limited to random access memory, read-only memory, programmable read-only memory, electrically programmable read-only memory, electrically erasable read-only memory, flash memory, magnetic tape or disk, optical media and the like. In one case, the memory 204 may include a cache or random access memory for the processor 202. Alternatively or in addition, the memory 204 may be separate from the processor 202, such as a cache memory of a processor, the system memory, or other memory. The memory 204 may be an external storage device or database for storing data. Examples may include a hard drive, compact disc ("CD"), digital video disc ("DVD"), memory card, memory stick, floppy disc, universal serial bus ("USB") memory device, or any other device operative to store data. The memory 204 may be operable to store instructions 224 executable by the processor 202. The functions, processes, acts or tasks illustrated in the figures or described herein may be performed by the programmed processor 202 executing the instructions 224 stored in the memory 204. Alternatively or in addition, the instructions 224 for carrying out the functions, process, acts or tasks described herein may be embedded in hardware, software, or some combination of both, such as ROM in the controller. The functions, processes, acts or tasks may be independent of the particular type of instructions set, storage media, processor or processing strategy and may be performed by software, hardware, integrated circuits, firmware, micro-code and the like, operating alone or in combination. Likewise, processing strategies may include multiprocessing, multitasking, parallel processing and the like.

The controller unit 200 may further include, or be in communication with, a display 210, such as a liquid crystal display (LCD), an organic light emitting diode (OLED), a flat panel display, a solid state display, a cathode ray tube (CRT), a projector, a printer or other now known or later developed display device for outputting determined information. The display 210 may act as an interface for the user to see the functioning of the processor 202, or specifically as an interface with the software stored in the memory 204 or in the drive unit 206.

Additionally, the controller unit 200 may include, or be in communication with, an input device 212 configured to allow a user to interact with any of the components of controller unit 200. The input device 212 may be a number pad, a keyboard, or a cursor control device, such as a mouse, or a joystick, touch screen display, remote control or any other device operative to interact with the controller unit 200. The input device 212 may be part of display 210.

The controller unit 200 may also include a disk or optical drive unit 206. The disk drive unit 206 may include a computer-readable medium 222 in which one or more sets of instructions 224, e.g. software, can be embedded. Further, the instructions 224 may perform one or more of the methods or logic as described herein. The instructions 224 may reside completely, or at least partially, within the memory 204 and/or within the processor 202 during execution by the controller unit 200. The memory 204 and the processor 202 also may include computer-readable media as discussed above.

The present disclosure contemplates a computer-readable medium 222 that includes instructions 224 or receives and executes instructions 224 responsive to a propagated signal; so that a device connected to a network 216 may communicate voice, video, audio, images or any other data over the network 216. Further, the instructions 224 may be transmitted or received over the network 216 via a communication interface 214. The communication interface 214 may be a part of the processor 202 or may be a separate component. The communication interface 214 may be created in software or may be a physical connection in hardware. The communication interface 214 may be configured to connect with a network 216, additional devices, external media, the display 210, or any other components in controller unit 200, or combinations thereof. The connection with the communication interface 214 may be a physical connection, such as a RS-232 connection, wired Ethernet connection, wireless connection as discussed below, or any other type of connection. Likewise, the additional connections with other components of the controller unit 200 may be physical connections or may be established wirelessly.

The network 216 may include additional devices used in conjunction with insufflation system 100, wired networks, wireless networks, or combinations thereof. The wireless network may be a cellular telephone network, an 802.11, 802.16, 802.20, or WiMax network. Further, the network 216 may be a public network, such as the Internet, a private network, such as an intranet, or combinations thereof, and may utilize a variety of networking protocols now available or later developed including, but not limited to TCP/IP based networking protocols.

The computer-readable medium 222 may be a single medium, or the computer-readable medium 222 may be a single medium or multiple media, such as a centralized or distributed database, and/or associated caches and servers that store one or more sets of instructions. The term "computer-readable medium" may also include any medium that may be capable of storing, encoding or carrying a set of instructions for execution by a processor or that may cause a computer system to perform any one or more of the methods or operations disclosed herein.

The computer-readable medium 222 may include a solid-state memory such as a memory card or other package that houses one or more non-volatile read-only memories. The computer-readable medium 222 also may be a random access memory or other volatile re-writable memory. Additionally, the computer-readable medium 222 may include a magneto-optical or optical medium, such as a disk or tapes or other storage device to capture carrier wave signals such as a signal communicated over a transmission medium. A digital file attachment to an e-mail or other self-contained information archive or set of archives may be considered a distribution medium that may be a tangible storage medium. Accordingly, the disclosure may be considered to include any one or more of a computer-readable medium or a distribution medium and other equivalents and successor media, in which data or instructions may be stored.

As is known in the art, insufflation system 100 may include additional components in order to operate the system and ensure patient safety. Insufflation system 100 includes pressure regulator 118. Pressure regulator 118 may reduce the pressure of the gas at the inlet of insufflation system 100 to a lower level to provide a safe operating pressure for a given surgical procedure, such as a laparoscopic procedure. Pressure regulator may be controlled by the controller unit 101 or may operate automatically. Pressure regulator 118 may include a pressure relief valve. Insufflation system 100 may include additional pressure relief valve 120 located upstream of the insufflation system 100 gas outlet to the patient. Pressure relief valve 120 may provide redundant pressure control of the gas delivered to the patient. Pressure relief valve 120 may be set to open and relieve pressure in the system if the gas pressure becomes too high. Insufflation system 100 includes filter 122. Filter 122 may remove particles from the gas connected to the inlet of insufflation system 100 to prevent particulate from damaging downstream equipment or being delivered to the patient. Filter 122 may be designed to remove certain micron sized particles depending on the application of the system.

Insufflation system 100 includes a branch to a separate gas line 124 that leads to a separate abdominal pressure measurement system (not shown) that works in conjunction with insufflation system 100. The separate abdominal pressure measurement system may measure the pressure in the patient's abdominal cavity through a line that is separate from the main gas delivery line to the patient in insufflation system 100. The separate abdominal pressure measurement system may measure the pressure in the patient's abdominal cavity while gas is delivered to the patient through the main gas delivery line in insufflation system 100. Accordingly, the pressure measured by the separate abdominal pressure measurement system is undistorted by the flow of gas being delivered to the patient in insufflation system 100. The separate abdominal pressure measurement system may send a small amount of gas intermittently or continuously down the separate gas line 124 in order to detect blockage or leakage in the separate abdominal pressure measurement system or downstream equipment, such as tubing, needles, or trocars. The separate abdominal pressure measurement system may share operating principles with U.S. Pat. No. 6,299,592, the entirety of which is hereby incorporated herein by reference. Insufflation system 100 includes valve 126 that affects the flow of gas to separate gas line 124 and the separate abdominal pressure measurement system. Valve 126 may be an on-off valve, variable orifice valve, or any other valve known to influence gas flow. Valve 126 may be electronically monitored and controlled by the controller unit 101.

Operation of insufflation system 100 will be described by referring to FIGS. 1, 3, and 4. The inlet of insufflation system 100 will be connected directly or indirectly to a high pressure source of gas. The outlet of insufflation system 100 will be connected directly or indirectly to a patient's abdominal cavity. Insufflation system 100 delivers gas from the high pressure source of gas to the patient's abdominal cavity in order to pressurize the abdominal cavity and achieve pneumoperitoneum. Pneumoperitoneum is typically achieved by pressurizing the abdominal cavity to 12-15 mmHg. Different pneumoperitoneum pressures may be used depending on various parameters, such as type of operation and/or type of patient. The pressure in the abdominal cavity is measured through pressure sensors (not shown) in the separate abdominal pressure measurement system or in insufflation system 100.

The controller unit 101 in insufflation system 100 varies the flow of gas to the abdominal cavity in order to establish or maintain the desired pneumoperitoneum pressure. Based on the gas flow requested, the controller unit 101 will select one of the flow rate sensors 102, 104, 106. By selecting a flow rate sensor, the controller unit 101 will utilize the output signal from the selected sensor when calculating the measured flow rate. The non-selected flow rate sensors may or may not continue to output signals to the controller unit 101. The selected flow rate sensor will have a flow rate range that corresponds to the requested flow. The controller unit 101 may select a flow rate sensor based on if the signals from the flow rate sensor are within an acceptable accuracy range. The controller unit 101 may determine the acceptable accuracy range based on testing or tuning of the insufflation system and/or components of the insufflation system. For example, if it is known that a flow rate sensor is accurate within a range of 1 to 8 liters per minute and the flow rate sensor is outputting a signal indicating the measured flow rate is 10 liters per minute, the controller unit 101 may select a flow rate sensor with a higher acceptable accuracy range. The readings from the flow rate sensor are related to the requested flow. The controller unit 101 will open the valve 114 associated with the selected flow rate sensor and will close the valves 114 associated with the non-selected flow rate sensor. Accordingly, gas will be delivered to the patient from the high pressure source through the selected flow rate sensor. For example, if the controller unit 101 requests a gas flow of 0.5 liters per minute to be delivered to the patient through controllable valve 116, the controller unit 101 may select flow rate sensor 102 which may have a flow rate range of 0 liters per minute to 1.1 liters per minute. The controller unit 101 will open valve 114 associated with flow rate sensor 102 and close the valves 114 associated with flow rate sensors 104 and 106. The gas flow from the high pressure source to the patient will flow through and be measured by flow rate sensor 102. The controller unit 101 will monitor the gas flow measured by flow rate sensor 102 in order to adjust controllable valve 116 to achieve the requested gas flow of 0.5 liters per minute. If the requested gas flow changes, the controller unit 101 may select a new flow rate sensor that has a flow rate range corresponding with the requested gas flow. Utilizing a flow rate sensor with a flow rate range that corresponds to the requested flow provides a more accurate flow rate measurement than using a flow rate sensor with a flow rate range outside of the requested flow.

Figure 3:
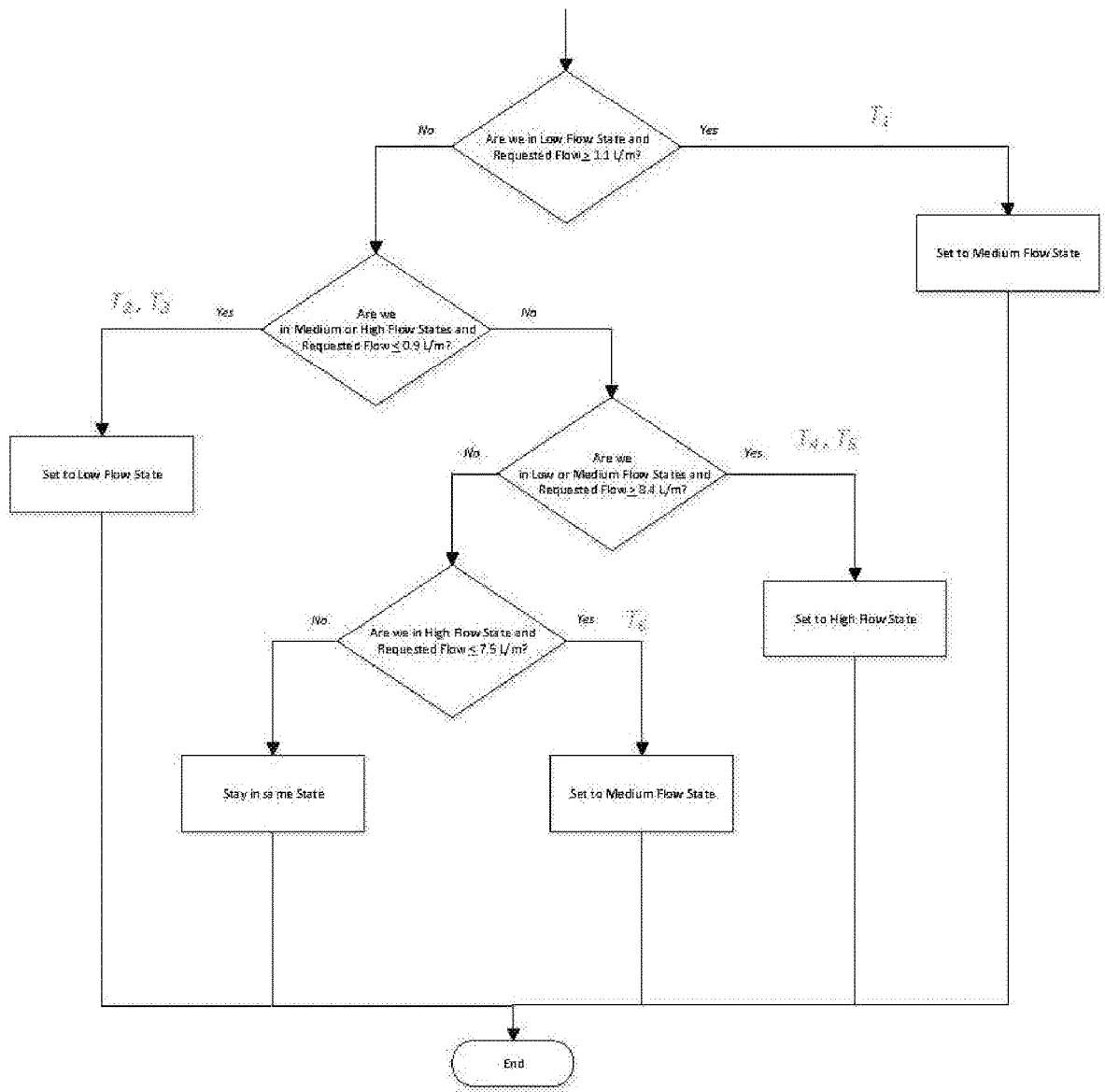
FIG. 3 is a decision flowchart used with an insufflation system according to an embodiment.

FIG. 3 is a decision flowchart that may be used with insufflation system 100 to select an appropriate flow rate sensor. The controller unit 101 may process through the flowchart in FIG. 3 many times a second, such as every 10 milliseconds, in order to ensure the most appropriate flow rate sensor is selected. FIG. 3 uses terminology such as low flow state, medium flow state, and high flow state to refer to low flow applications, medium flow applications, and high flow applications, respectively. The low flow state may utilize the low flow rate sensor 102, the medium flow state may utilize the medium flow rate sensor 104, and the high flow state may utilize the high flow rate sensor 106. The flow rates listed in FIG. 3 are exemplary and may vary based on the application. One of skill in the art will recognize that the logic path in FIG. 3 may vary depending on the application. For example, the flowchart may begin by determining if the system is operating in a high flow state with a requested flow of ≥8.4 liters per minute instead of determining if the system is operating in a low flow state with a requested flow of ≥1.1 liters per minute, as is shown in FIG. 3. The subsequent determinations may vary accordingly.

Figure 4:
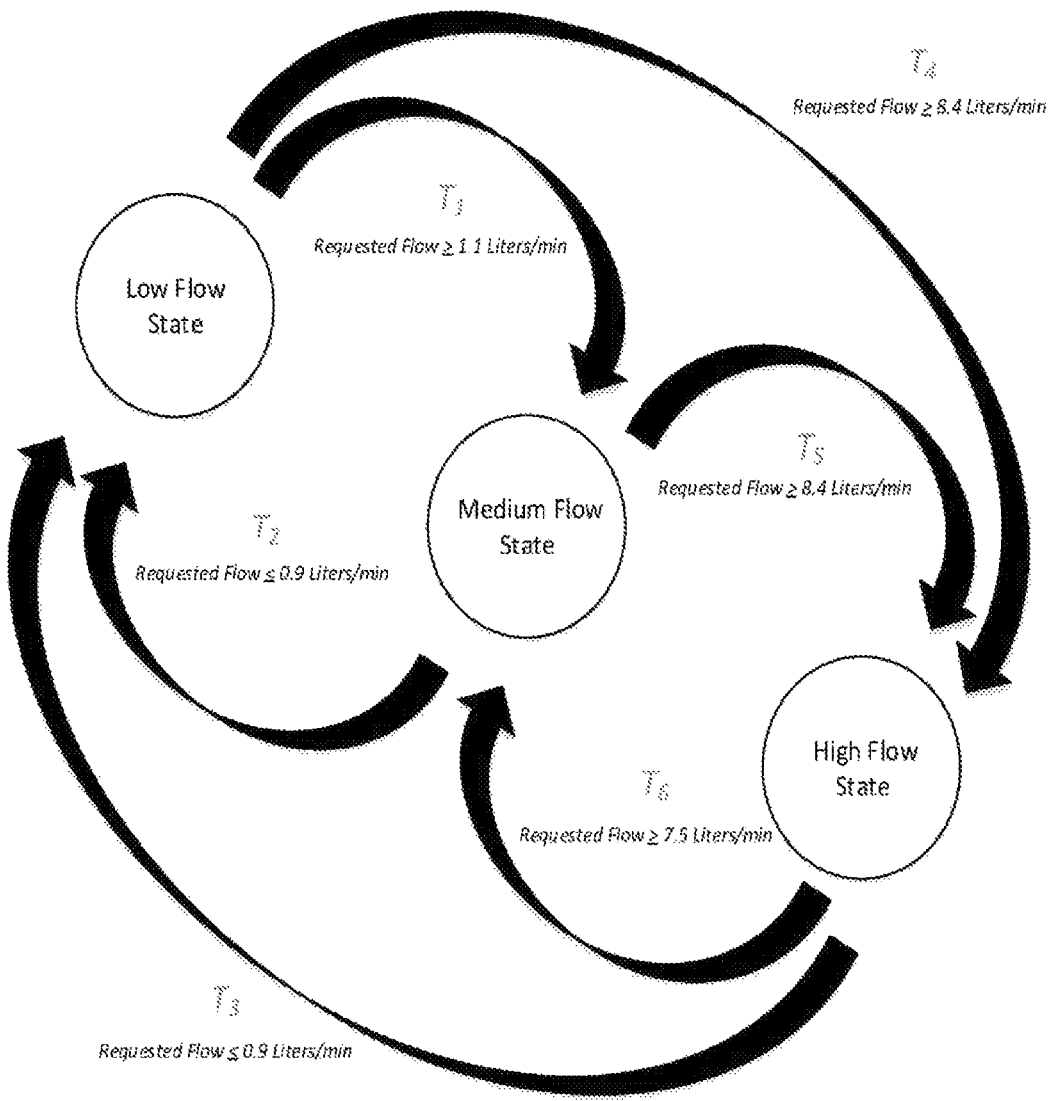
FIG. 4 is another decision flowchart used with an insufflation system according to an embodiment.

FIG. 4 is another decision flowchart that may be used with insufflation system 100 to select an appropriate flow rate sensor. As in FIG. 3, FIG. 4 uses terminology such as low flow state, medium flow state, and high flow state to refer to low flow applications, medium flow applications, and high flow applications, respectively. The low flow state may utilize the low flow rate sensor 102, the medium flow state may utilize the medium flow rate sensor 104, and the high flow state may utilize the high flow rate sensor 106. If the controller unit 101 is in the low flow state, the controller unit 101 may switch to the medium flow state if the requested flow is greater than or equal to 1.1 liters per minute and may switch to the high flow state if the requested flow is greater than or equal to 8.4 liters per minute. If the controller unit 101 is in the medium flow state, the controller unit 101 may switch to the low flow state if the requested flow is less than or equal to 0.9 liters per minute and may switch to the high flow state if the requested flow is greater than or equal to 8.4 liters per minute. If the controller unit 101 is in the high flow state, the controller unit 101 may switch to the low flow state if the requested flow is less than or equal to 0.9 liters per minute and may switch to the medium flow state if the requested flow is less than or equal to 7.5 liters per minute.

If the measured pressure in the abdominal cavity is far from the desired pneumoperitoneum pressure in the abdominal cavity, such as during initial insufflation or after a large gas loss from the abdomen, the controller unit 101 may request a relatively high gas flow to be delivered to the abdomen in order to most quickly reach the desired pressure. For example, referring to FIG. 4, if insufflation system 100 were in the low flow state and the controller unit 101 requested the maximum flow of the insufflator unit, such as 50 liters per minute or more, the controller unit 101 may follow path $T_4$ in order to change to the high flow state. The high flow state may utilize the flow rate sensor with the highest flow rate range, such as flow rate sensor 106, to measure the gas flow delivered to the patient through controllable valve 116. The controller unit 101 may adjust valves 114 in order to direct the gas flow through manifold 112 and through flow rate sensor 106. Subsequently, as the measured pressure in the abdominal cavity gets close to the desired pneumoperitoneum pressure, the controller unit 101 may request a relatively low gas flow to be delivered to the abdomen in order to prevent overpressurizing the patient. For example, referring to FIG. 4, if insufflation system 100 were in the high flow state and the controller unit 101 requested a gas flow of 10 liters per minute, the controller unit 101 may follow path T6 in order to change to the medium flow state. The medium flow state may utilize a flow rate sensor with an intermediate flow rate range, such as flow rate sensor 104, to measure the gas flow delivered to the patient through controllable valve 116. The controller unit 101 may adjust valves 114 in order to direct the gas flow through manifold 112 and through flow rate sensor 104. Maintaining high accuracy flow measurement as the measured pressure converges with the desired pneumoperitoneum pressure may prevent overpressurizing the patient. The controller unit 101 may request a gas flow of 0 liters per minute once the measured pressure in the abdominal cavity reaches the desired pneumoperitoneum pressure.

Figure 5:
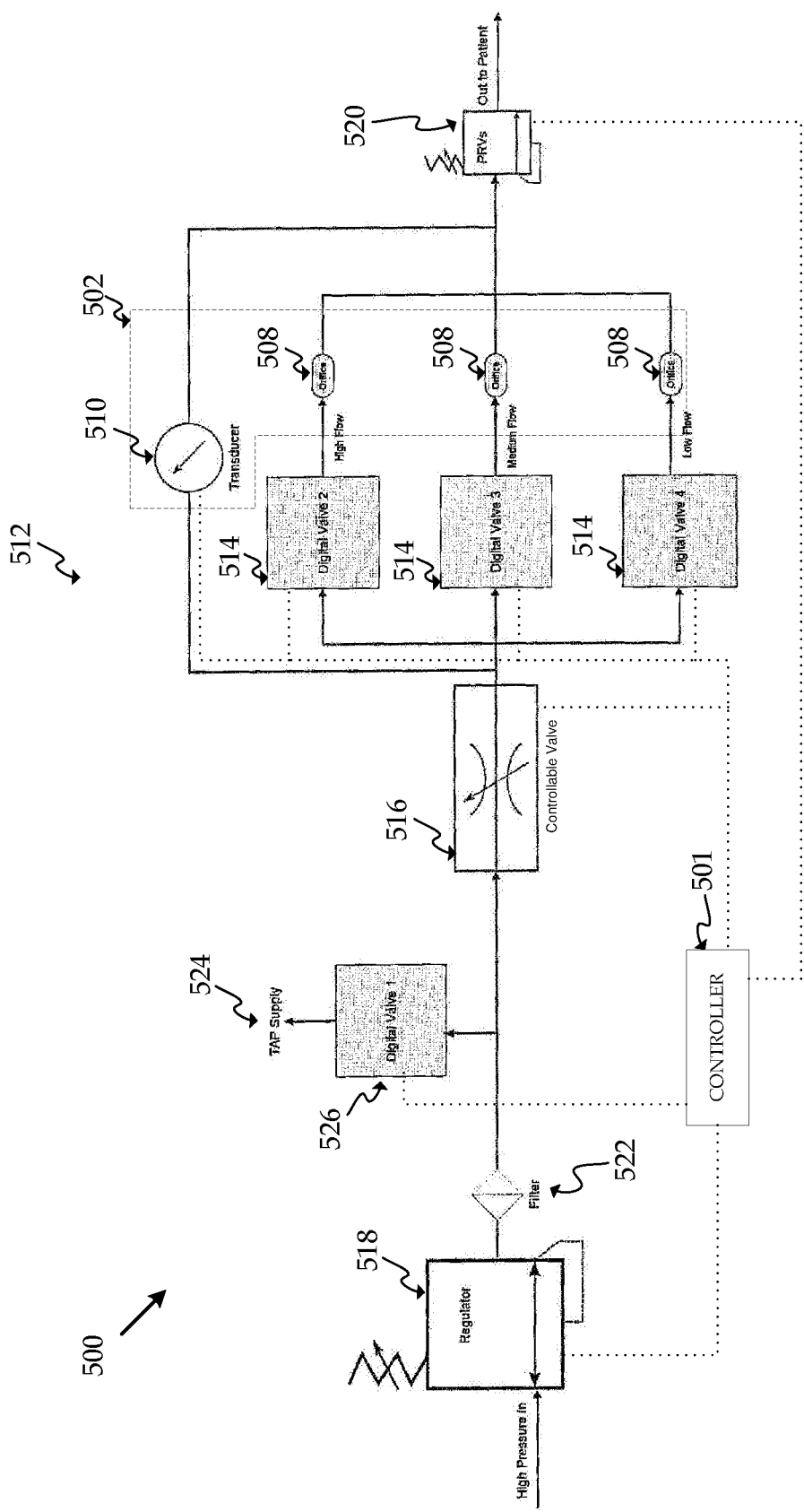
FIG. 5 is a block diagram of an insufflation system according to an embodiment.

FIG. 5 shows another embodiment, insufflation system 500. Insufflation system 500 may include some or all of the same elements as insufflation system 100. Similar elements will be referred to using the same last two digits as in FIG. 1. One of skill in the art will recognize that the function and operating characteristics of insufflation system 100 and its elements are applicable to insufflation system 500 and its elements, with minor changes based on differing location and number of certain elements. Insufflation system 500 includes controller unit 501, pressure regulator 518, filter 522, separate gas line 524, valve 526, controllable valve 516, manifold 512, valves 514, orifices 508, transducer 510, flow rate sensor 502, and pressure relief valve 520. Flow rate sensor 502 may utilize any of the orifices 508 and may include a single transducer 510.

Insufflation system 500 has one transducer 510 for use with flow rate sensor 502. Transducer 510 measures the pressure upstream and downstream of all orifices 508 for flow rate sensor 502. The controller unit 501 of insufflation system 500 will select one of the orifices 508 to be used in flow rate sensor 502 based on the gas flow requested to be delivered to the patient and the flow rate range of the orifice 508. Utilizing the orifice with a flow rate range that most closely corresponds with the requested flow rate will result in the most accurate flow rate measurement. The controller unit 501 will open the valve 514 associated with the selected orifice and will close the valves 514 associated with the non-selected orifice. Accordingly, gas will be delivered to the patient from the high pressure source through the selected orifice and flow rate sensor.

In insufflation system 500, controllable valve 516 is located upstream of flow rate sensor 502. The position of controllable valve 516 may be varied based on the system requirements, application, or manufacturer preference. The position of controllable valve 516 may affect the system, such as pneumatics or software, but various positions can achieve similar outcomes.

Operation of insufflation system 500 may be similar to operation of insufflation system 100. Insufflation system 500 may follow the decision flowcharts in FIGS. 3 and/or 4. Insufflation system 500 will improve the accuracy of the gas flow rate measurement to the patient through controllable valve 516 by selecting the orifice 508 for flow rate sensor 502 that corresponds with the requested flow rate. Insufflation system 500 may be less expensive to produce than insufflation system 100 because insufflation system 500 includes only one pressure transducer for the use with three orifices. However, the resolution of the flow rate measurement in insufflation system 500 may be lower than insufflation system 100 because the digital output data points in the single pressure transducer 510 are spread across the entire flow range capability of insufflation system 500, such as 0 to 50 liters per minute or more.

Figure 6:
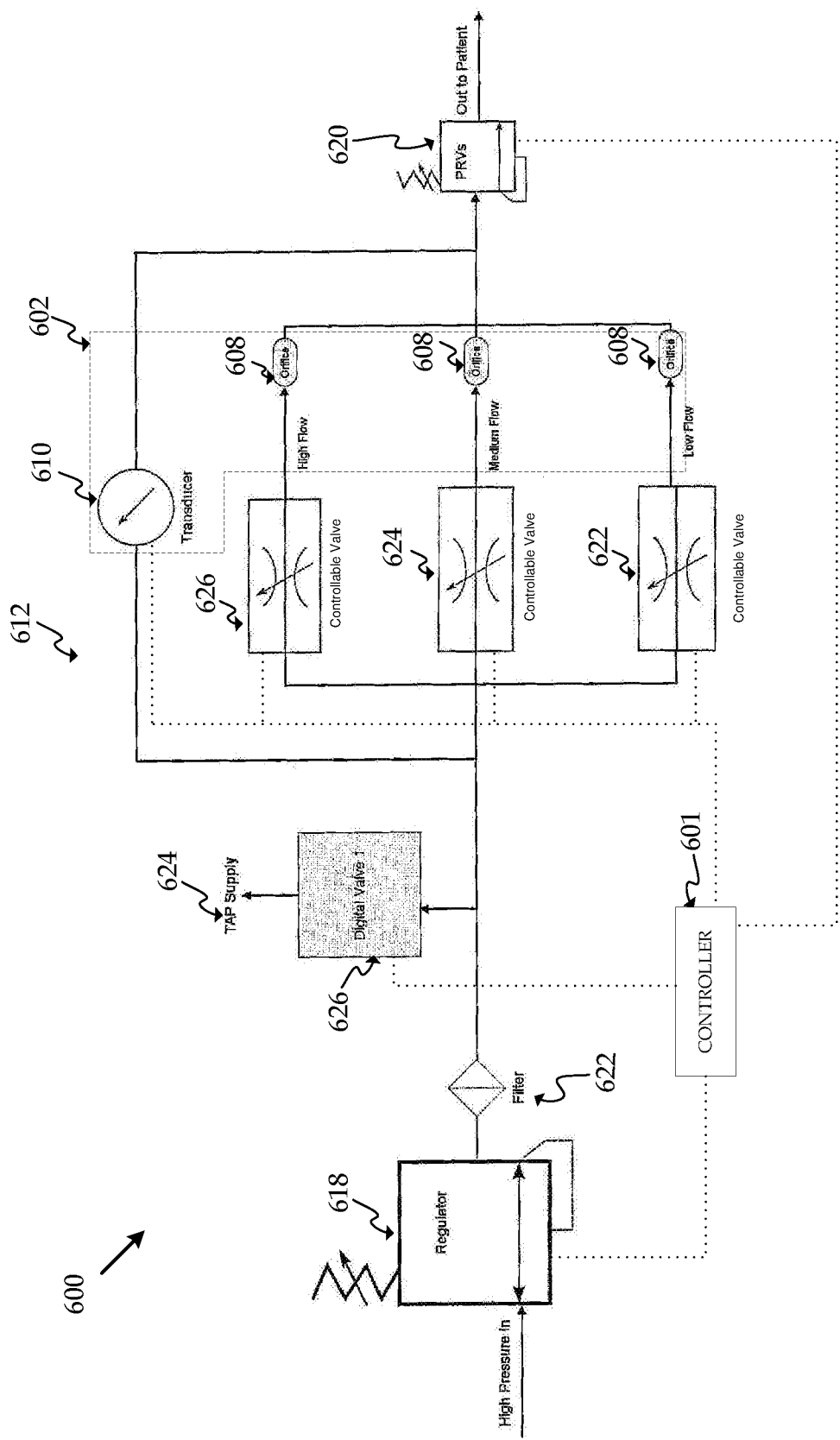
FIG. 6 is a block diagram of an insufflation system according to an embodiment.

FIG. 6 shows another embodiment, insufflation system 600. Insufflation system 600 may include some or all of the same elements as insufflation system 500. Similar elements will be referred to using the same last two digits as in FIG. 5. One of skill in the art will recognize that the function and operating characteristics of insufflation system 500 and its elements are applicable to insufflation system 600 and its elements, with minor changes based on differing location and number of certain elements. Insufflation system 600 includes controller unit 601, pressure regulator 618, filter 623, separate gas line 624, valve 626, manifold 612, orifices 608, transducer 610, flow rate sensor 602, pressure relief valve 620, and controllable valves 622, 624, and 626. Flow rate sensor 602 may utilize any of the orifices 608 and may include a single transducer 610.

Insufflation system 600 includes three controllable valves 622, 624, 626 for use with flow rate sensor 602. The size, type, and operating characteristics, such as trim, Cv, K, flow curves, travel, pressure drop, gain, of controllable valves 622, 624, 626 may be designed and optimized based on the flow rate range of flow rate sensor 602. The flow rate range of flow rate sensor 602 may vary depending on which orifice 608 is utilized. Alternatively, each of controllable valves 622, 624, 626 may be identical. Designing a controllable valve for narrower flow range may result in better control of the gas flow through the valve. Utilizing the flow rate sensor and controllable valve with flow rate ranges that most closely correspond with the requested flow rate will result in the most accurate flow rate measurement.

Operation of insufflation system 600 may be similar to operation of insufflation system 100. Insufflation system 600 may follow the decision flowcharts in FIGS. 3 and/or 4. Insufflation system 600 will improve the accuracy of the gas flow rate measurement to the patient by selecting the orifice 608 to be used with flow rate sensor 602 that corresponds with the requested flow rate. Insufflation system 600 may be more expensive to produce than insufflation system 500 because insufflation system 600 includes three controllable valves. However, the control of the gas flow to the patient in insufflation system 600 may be better than insufflation system 500 because the controllable valve in insufflation system 600 may be designed for a smaller flow range.

Figure 7:
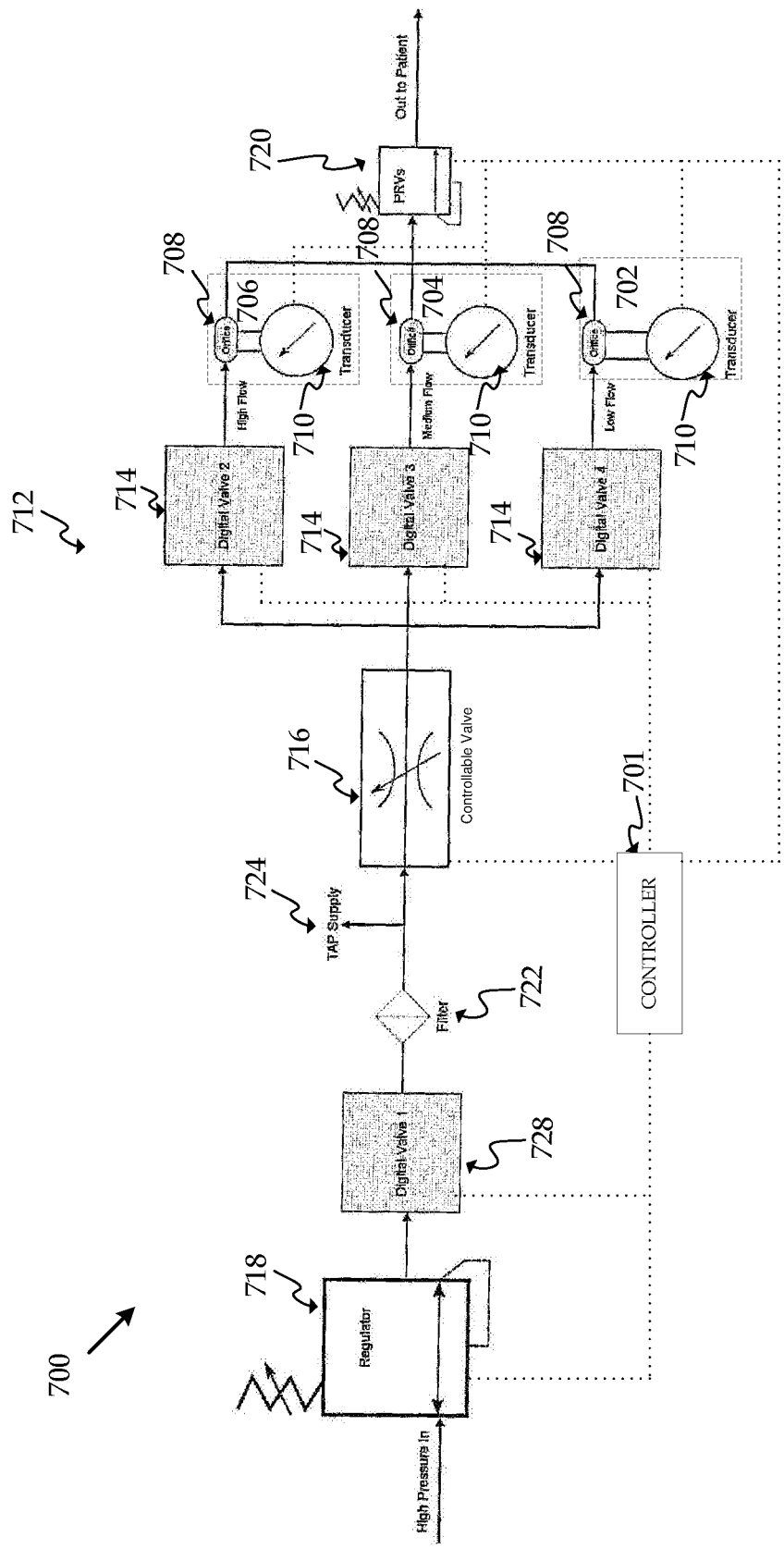
FIG. 7 is a block diagram of an insufflation system according to an embodiment.

FIG. 7 shows another embodiment, insufflation system 700. Insufflation system 700 may include some or all of the same elements as insufflation system 100. Similar elements will be referred to using the same last two digits as in FIG. 1. One of skill in the art will recognize that the function and operating characteristics of insufflation system 100 and its elements are applicable to insufflation system 700 and its elements, with minor changes based on differing location of certain elements. Insufflation system 700 includes controller unit 701, pressure regulator 718, filter 722, separate gas line 724, controllable valve 716, manifold 712, valves 714, orifices 708, transducers 710, flow rate sensors 702, 704, 706, pressure relief valve 720, and valve 728.

In insufflation system 700, controllable valve 716 is located upstream of flow rate sensors 702, 704, 707. The position of controllable valve 716 may be varied based on the system requirements, application, or manufacturer preference. The position of controllable valve 716 may affect the system, such as pneumatics or software, but various positions can achieve similar outcomes.

Insufflation system 700 includes valve 728. Valve 728 may be an on-off valve, variable orifice valve, or any other valve known to influence gas flow. Valve 728 may be electronically monitored and controlled by controller unit 701. The controller unit 701 may open or close valve 728 as necessary to affect the flow of gas in insufflation system 700. Valve 728 may be used to stop gas flow to the remainder of insufflation system 700 and also to the separate abdominal pressure measurement system through separate gas line 724.

Operation of insufflation system 700 may be similar to operation of insufflation system 100. Insufflation system 700 may follow the decision flowcharts in FIGS. 3 and/or 4. Insufflation system 700 will improve the accuracy of the gas flow rate measurement to the patient through controllable valve 716 by selecting the flow rate sensor 702, 704, 706 that corresponds with the requested flow rate.

Figure 8:
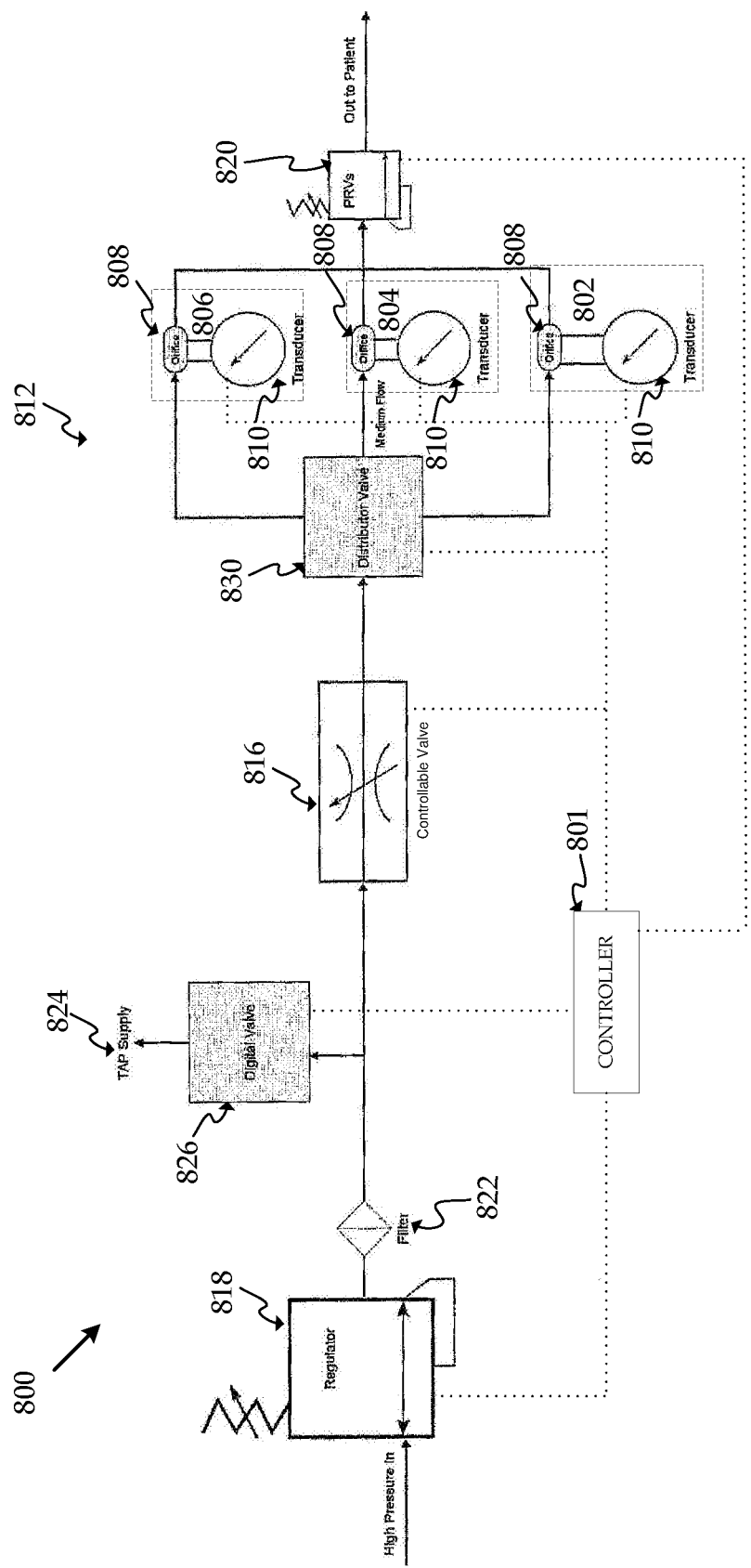
FIG. 8 is a block diagram of an insufflation system according to an embodiment.

FIG. 8 shows another embodiment, insufflation system 800. Insufflation system 800 may include some or all of the same elements as insufflation system 100. Similar elements will be referred to using the same last two digits as in FIG. 1. One of skill in the art will recognize that the function and operating characteristics of insufflation system 100 and its elements are applicable to insufflation system 800 and its elements, with minor changes based on differing location of and addition of certain elements. Insufflation system 800 includes controller unit 801, pressure regulator 818, filter 822, separate gas line 824, valve 826, controllable valve 816, manifold 812, orifices 808, transducers 810, flow rate sensors 802, 804, 806, pressure relief valve 820, and distributor valve 830.

In insufflation system 800, controllable valve 816 is located upstream of flow rate sensors 802, 804, 806. The position of controllable valve 816 may be varied based on the system requirements, application, or manufacturer preference. The position of controllable valve 816 may affect the system, such as pneumatics or software, but various positions can achieve similar outcomes.

Insufflation system 800 includes distributor valve 830. Distributor valve 830 has one inlet and three outlets in insufflation system 800. Alternatively, distributor valve 830 may have more or less inlets and outlets. Distributor valve 830 may be electronically monitored and controlled by controller unit 801. The controller unit 801 may adjust distributor valve 830 as necessary to direct the flow of gas in insufflation system 800 to one of flow rate sensors 802, 804, 806. Distributor valve 830 may be used to direct gas flow to a particular flow rate sensor or sensors and may be used to obstruct gas flow to a particular flow rate sensor or sensors. For example, the distributor valve 830 may open the flow path associated with flow rate sensor 802 and may simultaneously close the flow paths associated with flow rate sensors 804 and 806. Accordingly, the gas flow through flow rate sensor 802 will be the same as the gas flow delivered to the patient.

Operation of insufflation system 800 may be similar to operation of insufflation system 100. Insufflation system 800 may follow the decision flowcharts in FIGS. 3 and/or 4. Insufflation system 800 will improve the accuracy of the gas flow rate measurement to the patient through by selecting the flow rate sensor 802, 804, 806 that corresponds with the requested flow rate. Insufflation system 800 may be less expensive to produce than insufflation system 100 because insufflation system 800 includes a single distributor valve 830 instead of three valves 114 to distribute the gas flow to flow rate sensors 802, 804, 806.

Figure 9:
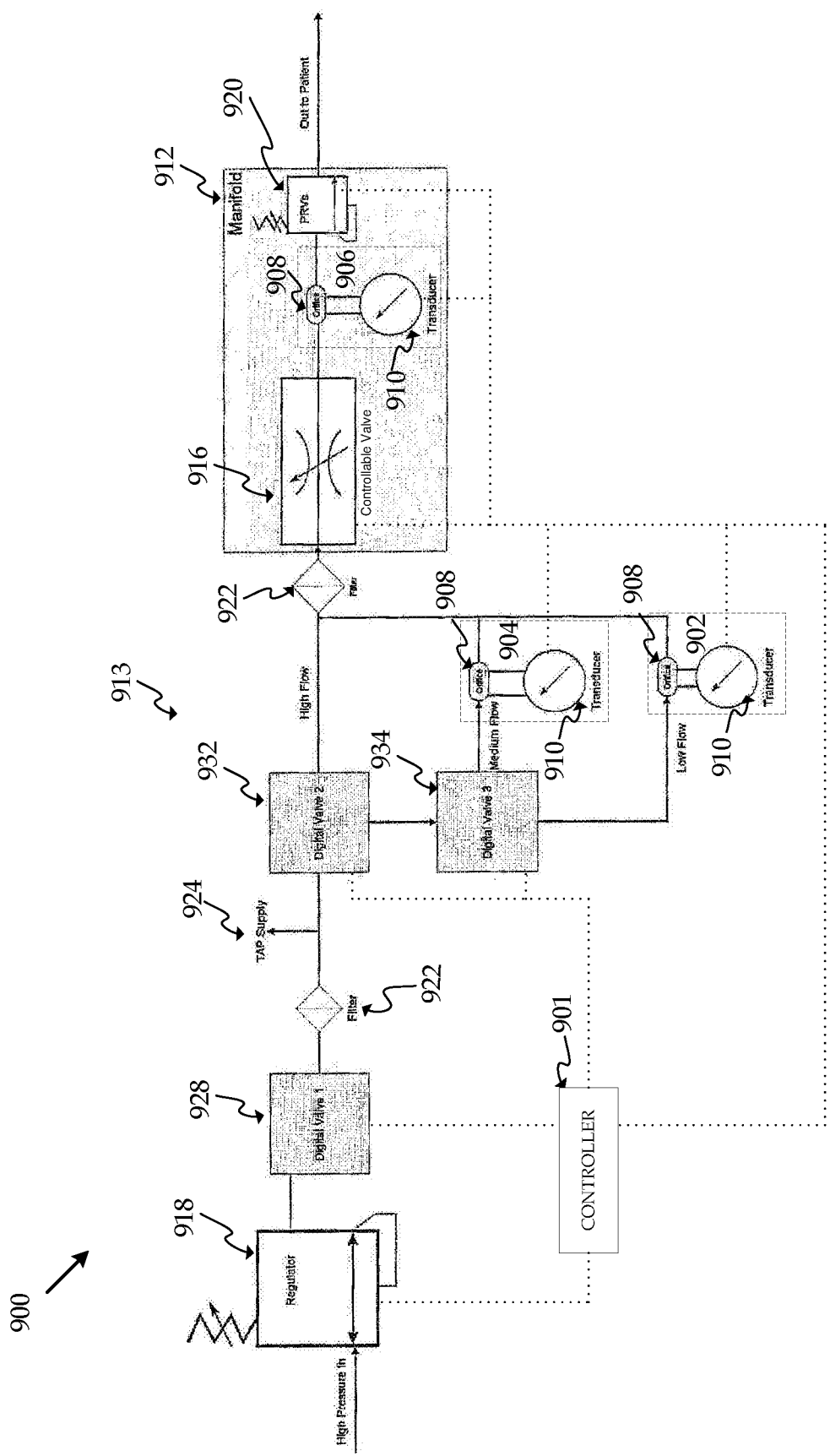
FIG. 9 is a block diagram of an insufflation system according to an embodiment.

FIG. 9 shows another embodiment, insufflation system 900. Insufflation system 900 may include some or all of the same elements as insufflation system 100. Similar elements will be referred to using the same last two digits as in FIG. 1. One of skill in the art will recognize that the function and operating characteristics of insufflation system 100 and its elements are applicable to insufflation system 900 and its elements, with changes based on differing location of certain elements. Insufflation system 900 includes controller unit 901, pressure regulator 918, filters 922, valve 928, separate gas line 924, controllable valve 916, manifolds 912, 913 orifices 908, transducers 910, flow rate sensors 902, 904, 906, pressure relief valve 920, and valves 932 and 934.

The gas distribution manifold in insufflation system 900 is divided into two manifolds 912 and 913. Manifolds 912 and 913 may be connected through tubing or other fluid communication methods. Components may be located between manifolds 912 and 913, such as filter 922. Alternatively, manifolds 912 and 913 may be joined or created from a single piece of material. Valves 932 and 934 distribute gas to manifolds 912 and 913. Valves 932 and 934 may be electronically monitored and controlled by controller unit 901. The controller unit 901 may adjust valves 932 and 934 as necessary to control the flow of gas to flow rate sensors 902, 904, and 906. For example, if the requested gas flow corresponds with the flow range of the high flow rate sensor, such as flow rate sensor 906, valve 932 will direct the gas flow to manifold 912 without passing through flow rate sensors 902 or 904. However, if the requested gas flow corresponds to the flow ranges of either the low or medium flow rate sensor, such as flow rate sensors 902 or 904, valve 932 will direct the gas flow to valve 934. Valve 934 will direct the gas flow to either the low or medium flow rate sensor, depending on which flow rate sensor has a flow range that corresponds to the requested gas flow.

As shown in FIG. 9, regardless of which flow rate sensor the controller unit 901 selects, the gas delivered to the patient through insufflation system 900 will pass through orifice 908 associated with flow rate sensor 906. The gas pressure drop through orifice 908 associated with flow rate sensor 906 is relatively small because flow rate sensor 906 is the high flow rate sensor in insufflation system 900, therefore orifice 908 associated with flow rate sensor 906 will be relatively large.

Operation of insufflation system 900 may be similar to operation of insufflation system 100. Insufflation system 900 may follow the decision flowcharts in FIGS. 3 and/or 4. Insufflation system 900 will improve the accuracy of the gas flow rate measurement to the patient through controllable valve 916 by selecting the flow rate sensor 902, 904, 906 that corresponds with the requested flow rate. Insufflation system 900 may be less expensive to manufacturer and assemble than insufflation system 100 due to the reduced number of valves in insufflation system 900. Insufflation system 900 includes two valves 932 and 934 to direct the gas flow to the appropriate flow rate sensor, whereas other embodiments may include three valves. Using fewer valves is less expensive, requires less electronics to power and monitor the valves, and allows for simpler control systems because there are fewer components to control.

Figure 10:
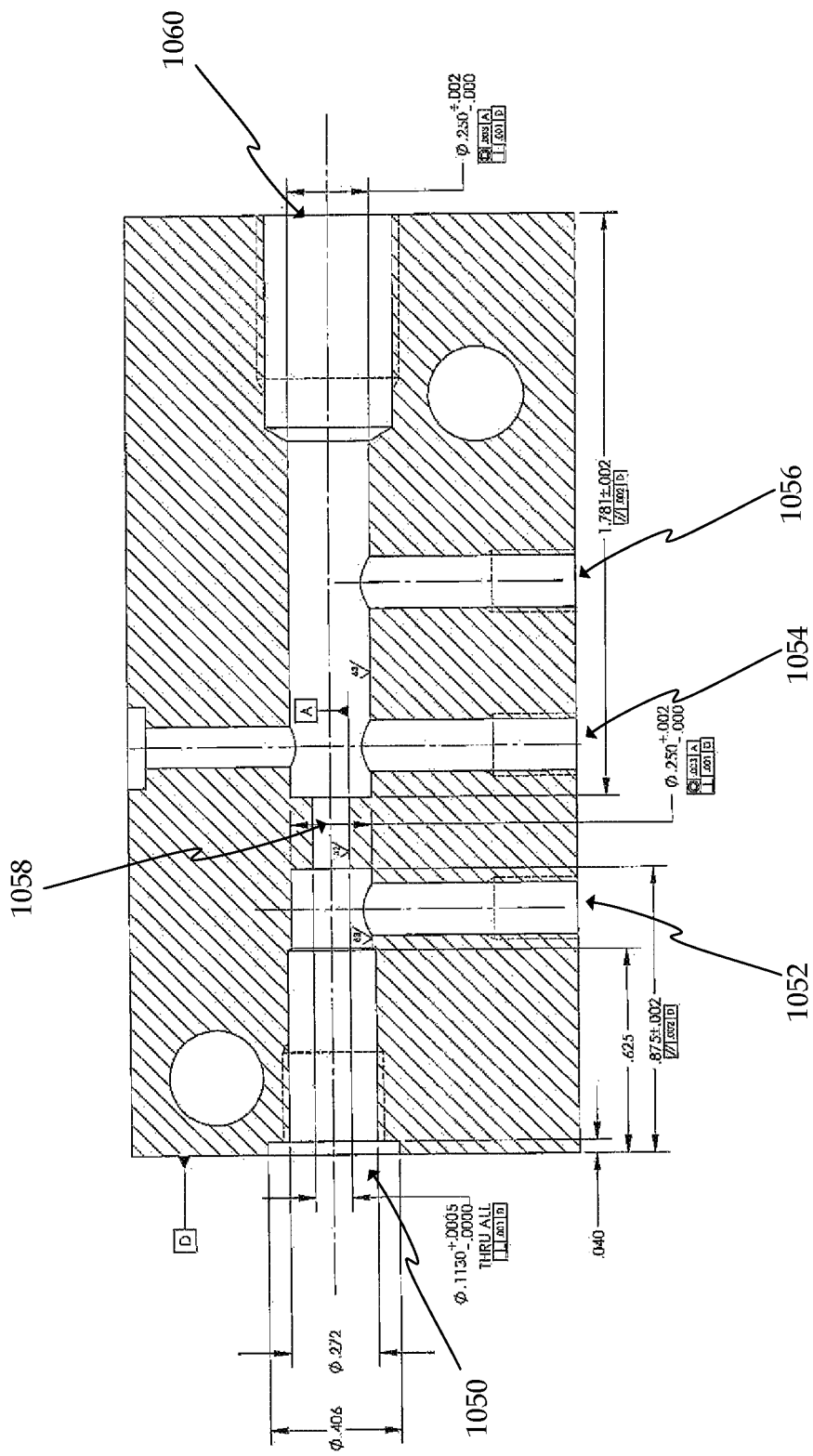
FIG. 10 is a cross-sectional view of a manifold according to an embodiment.

FIG. 10 shows an example embodiment of manifold 912. FIG. 10 is a cross-sectional view of the bottom half of manifold 912. The dimensions and number of openings shown in FIG. 10 are exemplary and may be varied as necessary for the application of the insufflation system. Opening 1050 is the gas inlet path to manifold 912. Openings 1052 and 1054 are the pressure transducer measurement ports. Opening 1056 is a port for a redundant pressure transducer associated with flow rate sensor 906. Orifice 1058 is the orifice associated with flow rate sensor 906. Orifice 1058 may be sized based on the flow range of flow rate sensor 906, which is the high flow rate sensor in insufflation system 900. Orifice 1058 may be machined from or built directly into manifold 912. Opening 1060 is the gas outlet path of manifold 912.

FIG. 11 shows an example embodiment of manifold 913. FIGS. 11A-11H show several perspective, planar, and cross-sectional views of manifold 913. Opening 1162 is the medium flow gas inlet path to manifold 913. Opening 1164 is the low flow gas inlet path to manifold 913. Openings 1166 and 1168 are the pressure transducer measurement ports for the medium flow rate sensor. Openings 1170 and 1172 are the pressure transducer measurement ports for the low flow rate sensor. Opening 1174 is the medium flow gas outlet path of manifold 912. Opening 1176 is the low flow gas outlet path of manifold 912. Orifice 1178 (two places) is the orifice associated with the medium flow rate sensor, which is flow rate sensor 904 in insufflation system 900. Orifice 1178 may be sized based on the flow range of flow rate sensor 904. Orifice 1180 (two places) is the orifice associated with the low flow rate sensor, which is flow rate sensor 902 in insufflation system 900. Orifice 1180 may be sized based on the flow range of flow rate sensor 902. Orifices 1178 and 1180 may be machined from or built directly into manifold 913.

Additional embodiments may be included that utilize two flow rate ranges, such as low flow and medium flow. The embodiment may switch between low flow and high flow around 4 liters per minute. Other flow rates may be used to switch between flow rate ranges as dictated by the operating requirements. Embodiments with two flow rate ranges may have a lower resolution than embodiments with three or more flow rate range, however embodiments with two flow rate ranges may achieve acceptable levels of resolution for insufflation systems with flow rate capability of 0.1 liters per minute to 50 liters per minute or more. FIGS. 12-17 disclose embodiments with two flow rate ranges.

FIG. 12 shows another embodiment, insufflation system 1200. Insufflation system 1200 may include some or all of the same elements as insufflation system 900. Similar elements will be referred to using the same last two digits as in FIG. 9. Insufflation system 1200 may include two flow rate ranges, such as for example, low flow and high flow. One of skill in the art will recognize that the function and operating characteristics of insufflation system 900 and its elements are applicable to insufflation system 1200 and its elements, with changes based on differing location and number of certain elements. Insufflation system 1200 includes controller unit 1201, pressure regulator 1218, filters 1222, valve 1228, separate gas line 1224, controllable valve 1216, manifolds 1212, 1213 orifices 1208, transducers 1210, flow rate sensors 1202, 1204, pressure relief valve 1220, and valve 1232.

The gas distribution manifold in insufflation system 1200 is divided into two manifolds 1212 and 1213. Manifolds 1212 and 1313 may be connected through tubing or other fluid communication methods. Components may be located between manifolds 1212 and 1213, such as filter 1222. Alternatively, manifolds 1212 and 1213 may be joined or created from a single piece of material. Valve 1232 distributes gas to manifolds 1212 and 1213. Valve 1232 may be electronically monitored and controlled by controller unit 1201. The controller unit 1201 may adjust valve 1232 as necessary to control the flow of gas to flow rate sensors 1202 and 1204. For example, if the requested gas flow corresponds with the flow range of the high flow rate sensor, such as flow rate sensor 1204, valve 1232 will direct the gas flow to manifold 1212 without passing through flow rate sensors 1202. However, if the requested gas flow corresponds to the flow ranges of the low flow rate sensor, such as flow rate sensors 1202, valve 1232 will direct the gas flow to flow rate sensors 1202.

As shown in FIG. 12, regardless of which flow rate sensor the controller unit 1201 selects, the gas delivered to the patient through insufflation system 1200 will pass through orifice 1208 associated with flow rate sensor 1204. The gas pressure drop through orifice 1208 associated with flow rate sensor 1204 is relatively small because flow rate sensor 1204 is the high flow rate sensor in insufflation system 1200, therefore orifice 1208 associated with flow rate sensor 1204 will be relatively large.

Operation of insufflation system 1200 may be similar to operation of insufflation system 900. Insufflation system 1200 may follow the decision flowcharts in FIGS. 3 and/or 4, with modifications made for two gas flow paths/states. Insufflation system 1200 will improve the accuracy of the gas flow rate measurement to the patient through controllable valve 1216 by selecting the flow rate sensor 1202, 1204 that corresponds with the requested flow rate. Insufflation system 1200 may be less expensive to manufacturer and assemble than insufflation system 900 due to the reduced number of valves and flow rate sensors in insufflation system 1200. Insufflation system 1200 includes one valve 1204 to direct the gas flow to the appropriate one of two flow rate sensors, whereas other embodiments may include two or three valves and three flow rate sensors. Using fewer valves and flow rate sensors is less expensive, requires less electronics to power and monitor the valves and sensors, and allows for simpler control systems because there are fewer components to control.

FIG. 13 shows another embodiment, insufflation system 1300. Insufflation system 1300 may include some or all of the same elements as insufflation system 700. Similar elements will be referred to using the same last two digits as in FIG. 7. Insufflation system 1300 may include two flow rate ranges, such as for example, low flow and high flow. One of skill in the art will recognize that the function and operating characteristics of insufflation system 700 and its elements are applicable to insufflation system 1300 and its elements, with minor changes based on differing location and number of certain elements. Insufflation system 1300 includes controller unit 1301, pressure regulator 1318, filter 1322, separate gas line 1324, controllable valve 1316, manifold 1312, valves 1314, orifices 1308, transducers 1310, flow rate sensors 1302, 1304, pressure relief valve 1320, and valve 1328.

In insufflation system 1300, controllable valve 1316 is located upstream of flow rate sensors 1302, 1304. The position of controllable valve 1316 may be varied based on the system requirements, application, or manufacturer preference. The position of controllable valve 1316 may affect the system, such as pneumatics or software, but various positions can achieve similar outcomes.

Insufflation system 1300 includes valve 1328. Valve 1328 may be an on-off valve, variable orifice valve, or any other valve known to influence gas flow. Valve 1328 may be electronically monitored and controlled by controller unit 1301. The controller unit 1301 may open or close valve 1328 as necessary to affect the flow of gas in insufflation system 1300. Valve 1328 may be used to stop gas flow to the remainder of insufflation system 1300 and also to the separate abdominal pressure measurement system through separate gas line 1324.

Operation of insufflation system 1300 may be similar to operation of insufflation system 700. Insufflation system 1300 may follow the decision flowcharts in FIGS. 3 and/or 4, with modifications made for two gas flow paths/states. Insufflation system 1300 will improve the accuracy of the gas flow rate measurement to the patient through controllable valve 1316 by selecting the flow rate sensor 1302, 1304 that corresponds with the requested flow rate.

FIG. 14 shows another embodiment, insufflation system 1400. Insufflation system 1400 may include some or all of the same elements as insufflation system 800. Similar elements will be referred to using the same last two digits as in FIG. 8. Insufflation system 1400 may include two flow rate ranges, such as for example, low flow and high flow. One of skill in the art will recognize that the function and operating characteristics of insufflation system 800 and its elements are applicable to insufflation system 1400 and its elements, with minor changes based on differing location of and addition/deletion of certain elements. Insufflation system 1400 includes controller unit 1401, pressure regulator 1418, filter 1422, separate gas line 1424, valve 1426, controllable valve 1416, manifold 1412, orifices 1408, transducers 1410, flow rate sensors 1402, 1404, pressure relief valve 1420, and distributor valve 1430.

In insufflation system 1400, controllable valve 1416 is located upstream of flow rate sensors 1402, 1404. The position of controllable valve 1416 may be varied based on the system requirements, application, or manufacturer preference. The position of controllable valve 1416 may affect the system, such as pneumatics or software, but various positions can achieve similar outcomes.

Insufflation system 1400 includes distributor valve 1430. Distributor valve 1430 has one inlet and two outlets in insufflation system 1400. Alternatively, distributor valve 1430 may have more or less inlets and outlets. Distributor valve 1430 may be electronically monitored and controlled by controller unit 1401. The controller unit 1401 may adjust distributor valve 1430 as necessary to direct the flow of gas in insufflation system 1400 to one of flow rate sensors 1402, 1404. Distributor valve 1430 may be used to direct gas flow to a particular flow rate sensor or sensors and may be used to obstruct gas flow to a particular flow rate sensor or sensors. For example, the distributor valve 1430 may open the flow path associated with flow rate sensor 1402 and may simultaneously close the flow path associated with flow rate sensor 1404. Accordingly, the gas flow through flow rate sensor 1402 will be the same as the gas flow delivered to the patient.

Operation of insufflation system 1400 may be similar to operation of insufflation system 800. Insufflation system 1400 may follow the decision flowcharts in FIGS. 3 and/or 4, with modifications made for two gas flow paths/states. Insufflation system 1400 will improve the accuracy of the gas flow rate measurement to the patient through by selecting the flow rate sensor 1402, 1404 that corresponds with the requested flow rate. Insufflation system 1400 may be less expensive to produce than insufflation system 800 because insufflation system 1400 includes two flow rate sensors 1402, 1404.

FIG. 15 shows another embodiment, insufflation system 1500. Insufflation system 1500 may include some or all of the same elements as insufflation system 500. Similar elements will be referred to using the same last two digits as in FIG. 5. Insufflation system 1500 may include two flow rate ranges, such as for example, low flow and high flow. One of skill in the art will recognize that the function and operating characteristics of insufflation system 500 and its elements are applicable to insufflation system 1500 and its elements, with minor changes based on differing location and number of certain elements. Insufflation system 1500 includes controller unit 1501, pressure regulator 1518, filter 1522, separate gas line 1524, valve 1526, controllable valve 1516, manifold 1512, valves 1514, orifices 1508, transducer 1510, flow rate sensor 1502, and pressure relief valve 1520. Flow rate sensor 1502 may utilize any of the orifices 1508 and may include a single transducer 1510.

Insufflation system 1500 has one transducer 1510 for use with flow rate sensor 1502. Transducer 1510 measures the pressure upstream and downstream of all orifices 1508 for flow rate sensor 1502. The controller unit 1501 of insufflation system 1500 will select one of the orifices 1508 to be used in flow rate sensor 1502 based on the gas flow requested to be delivered to the patient and the flow rate range of the orifice 1508. Utilizing the orifice with a flow rate range that most closely corresponds with the requested flow rate will result in the most accurate flow rate measurement. The controller unit 1501 will open the valve 1514 associated with the selected orifice and will close the valves 1514 associated with the non-selected orifice. Accordingly, gas will be delivered to the patient from the high pressure source through the selected orifice and flow rate sensor.

In insufflation system 1500, controllable valve 1516 is located upstream of flow rate sensor 1502. The position of controllable valve 1516 may be varied based on the system requirements, application, or manufacturer preference. The position of controllable valve 1516 may affect the system, such as pneumatics or software, but various positions can achieve similar outcomes.

Operation of insufflation system 1500 may be similar to operation of insufflation system 500. Insufflation system 1500 may follow the decision flowcharts in FIGS. 3 and/or 4 with modifications made for two gas flow paths/states. Insufflation system 1500 will improve the accuracy of the gas flow rate measurement to the patient through controllable valve 1516 by selecting the orifice 1508 for flow rate sensor 1502 that corresponds with the requested flow rate. Insufflation system 1500 may be less expensive to produce than insufflation system 100 because insufflation system 1500 includes only one pressure transducer for the use with two orifices. However, the resolution of the flow rate measurement in insufflation system 1500 may be lower than insufflation system 100 because the digital output data points in the single pressure transducer 1510 are spread across the entire flow range capability of insufflation system 1500, such as 0 to 50 liters per minute or more.

FIG. 16 shows another embodiment, insufflation system 1600. Insufflation system 1600 may include some or all of the same elements as insufflation system 600. Similar elements will be referred to using the same last two digits as in FIG. 6. Insufflation system 1600 may include two flow rate ranges, such as for example, low flow and high flow. One of skill in the art will recognize that the function and operating characteristics of insufflation system 600 and its elements are applicable to insufflation system 1600 and its elements, with minor changes based on differing location and number of certain elements. Insufflation system 1600 includes controller unit 1601, pressure regulator 1618, filter 1623, separate gas line 1624, valve 1626, manifold 1612, orifices 1608, transducer 1610, flow rate sensor 1602, pressure relief valve 1620, and controllable valves 1622, 1624. Flow rate sensor 1602 may utilize any of the orifices 1608 and may include a single transducer 1610.

Insufflation system 1600 includes two controllable valves 1622, 1624 for use with flow rate sensor 1602. The size, type, and operating characteristics, such as trim, Cv, K, flow curves, travel, pressure drop, gain, of controllable valves 1622, 1624 may be designed and optimized based on the flow rate range of flow rate sensor 1602. The flow rate range of flow rate sensor 1602 may vary depending on which orifice 1608 is utilized. Alternatively, each of controllable valves 1622, 1624 may be identical. Designing a controllable valve for narrower flow range may result in better control of the gas flow through the valve. Utilizing the flow rate sensor and controllable valve with flow rate ranges that most closely correspond with the requested flow rate will result in the most accurate flow rate measurement.

Operation of insufflation system 1600 may be similar to operation of insufflation system 600. Insufflation system 1600 may follow the decision flowcharts in FIGS. 3 and/or 4, with modifications made for two gas flow paths/states. Insufflation system 1600 will improve the accuracy of the gas flow rate measurement to the patient by selecting the orifice 1608 to be used with flow rate sensor 1602 that corresponds with the requested flow rate. Insufflation system 1600 may be more expensive to produce than insufflation system 1500 because insufflation system 1600 includes three controllable valves. However, the control of the gas flow to the patient in insufflation system 1600 may be better than insufflation system 1500 because the controllable valve in insufflation system 1600 may be designed for a smaller flow range.

FIG. 17 shows another embodiment, insufflation system 1700. Insufflation system 1700 may include some or all of the same elements as insufflation system 100. Similar elements will be referred to using the same last two digits as in FIG. 1. Insufflation system 1700 may include two flow rate ranges, such as for example, low flow and high flow. One of skill in the art will recognize that the function and operating characteristics of insufflation system 100 and its elements are applicable to insufflation system 1700 and its elements, with minor changes based on differing location and number of certain elements. Insufflation system 1700 includes controller unit 1701, pressure regulator 1718, filter 1722, separate gas line 1724, controllable valve 1716, manifold 1712, valves 1714, orifices 1708, transducers 1710, flow rate sensors 1702, 704, pressure relief valve 1720, and valve 1726.

In insufflation system 1700, controllable valve 1716 is located downstream of flow rate sensors 1702, 1704. The position of controllable valve 1716 may be varied based on the system requirements, application, or manufacturer preference. The position of controllable valve 1716 may affect the system, such as pneumatics or software, but various positions can achieve similar outcomes.

Operation of insufflation system 1700 may be similar to operation of insufflation system 100. Insufflation system 1700 may follow the decision flowcharts in FIGS. 3 and/or 4, with modifications made for two gas flow paths/states. Insufflation system 1700 will improve the accuracy of the gas flow rate measurement to the patient through controllable valve 1716 by selecting the flow rate sensor 1702, 1704 that corresponds with the requested flow rate.

The flow rates may be calculated by a controller, such as controller unit 200, using the following equation: Flow=Gain*(((Counts−Offset)^0.5)/10,000,000). The Gain and Offset are calibrated values from the flow rate sensor. The Counts is the current A to D counts. Each flow rate path may have different values for Gain and Offset. The A to D converter has 24 bits, therefore the counts vary from 0 to 2^24-1. The resolution of a flow rate sensor may be determined and graphed across flow rates and counts.

FIGS. 18-22 show exemplary graphs of various flow rate sensor resolution as functions of flow and counts per flow. The graphs show the amount of flow as a function of A to D counts and A to D counts for a particular granularity of flow, such as 0.01 liters per minute.

FIG. 18A shows an exemplary graph of calculated flow versus A to D counts for a low flow path in an embodiment with three flow paths. FIG. 18B shows an exemplary graph of counts per flow versus A to D counts for a low flow path in an embodiment with three flow paths. FIG. 19A shows an exemplary graph of calculated flow versus A to D counts for a medium flow path in an embodiment with three flow paths.

FIG. 19B shows an exemplary graph of counts per flow versus A to D counts for a medium flow path in an embodiment with three flow paths. FIG. 20A shows an exemplary graph of calculated flow versus A to D counts for a high flow path in an embodiment with three flow paths. FIG. 20B shows an exemplary graph of counts per flow versus A to D counts for a high flow path in an embodiment with three flow paths. FIG. 21A shows an exemplary graph of calculated flow versus A to D counts for a low flow path in an embodiment with two flow paths. FIG. 21B shows an exemplary graph of counts per flow versus A to D counts for a low flow path in an embodiment with two flow paths. FIG. 22A shows an exemplary graph of calculated flow versus A to D counts for a high flow path in an embodiment with two flow paths. FIG. 22B shows an exemplary graph of counts per flow versus A to D counts for a high flow path in an embodiment with two flow paths. FIGS. 21A, 21B and 22A, 22B show that a two flow path embodiment may provide an adequate level of flow rate resolution.

While various embodiments of the invention have been described, it will be apparent to those of ordinary skill in the art that many more embodiments and implementations are possible within the scope of the invention. The elements of the various embodiments disclosed may be combined and adapted to create a system with some or all of the operating characteristics and advantages of the embodiments. Any such combinations are herein disclosed in this application.

The invention claimed is:

1. An insufflation system configured for surgical use with a patient comprising:
   a plurality of flow rate sensors, wherein each of the flow rate sensors is configured to measure flow across a different flow rate range;
   a first valve in fluid communication with the plurality of flow rate sensors and a primary gas delivery line that is connectable to the patient;
   a controller configured to select one of the plurality of flow rate sensors based on a desired flow through the first valve; and
   wherein flow to non-selected flow rate sensors is obstructed by on-off valves, separate from the first valve, in fluid communication with each of the plurality of flow rate sensors.

2. The insufflation system of claim 1 wherein the controller selects one of the plurality of flow rate sensors based on a desired flow through the first valve and a selected one of the plurality of flow rate sensors.

3. The insufflation system of claim 1 wherein a combination of all the different flow rate ranges of the plurality of flow rate sensors encompasses flow rates of 0.1 liters per minute and 50 liters per minute.

4. The insufflation system of claim 1 wherein the desired flow through the first valve is determined by the controller based on a desired pressure in a patient's abdominal cavity and a current pressure detected in a patient's abdominal cavity, wherein the current pressure in the patient's abdominal cavity is measured through a pressure sensing line that is separate from the primary gas delivery line or is measured through the primary gas delivery line.

5. The insufflation system of claim 1 wherein the controller is in communication with the first valve and wherein the controller is configured to regulate the first valve to control a flow rate through the first valve.

6. The insufflation system of claim 1 wherein the first valve is a controllable valve.

7. The insufflation system of claim 1 wherein each of the plurality of flow rate sensors comprises an orifice and a pressure transducer.

8. The insufflation system of claim 1 wherein each of the plurality of flow rate sensors comprises two pressure transducers.

9. The insufflation system of claim 1 wherein the plurality of flow rate sensors comprise a first flow rate sensor, a second flow rate sensor, and a third flow rate sensor.

10. The insufflation system of claim 9 wherein the first flow rate sensor is configured to measure flow in a first flow rate range, the second flow rate sensor is configured to measure flow in a second flow rate range, third flow rate sensor is configured to measure flow in a third flow rate range, and wherein a segment of the first flow rate range is lower than a segment of the second flow rate range and a segment of the third flow rate range is higher than a segment the second flow rate range.

11. The insufflation system of claim 10 wherein a measured flow through the first valve is within 30 percent of the desired flow through the first valve when the desired flow is within the first flow rate range.

12. The insufflation system of claim 1 wherein a number of digital output data points available in each of the plurality of flow rate sensors is distributed across the flow rate range for each individual flow rate sensor.

13. The insufflation system of claim 12 wherein each of the plurality of flow rate sensors has at least 38,000 digital output data points available.

14. An insufflation system configured for surgical use with a patient comprising:
    a plurality of flow rate sensors, wherein each of the flow rate sensors is configured to measure flow across a different flow rate range;
    a first valve in fluid communication with the plurality of flow rate sensors and a primary gas delivery line that is connectable to the patient;
    a controller configured to select one of the plurality of flow rate sensors based on a desired flow through the first valve; and
    wherein each of the different flow rate ranges of the plurality of flow rate sensors only partially overlaps at least one adjacent flow rate range of the different flow rate ranges.

15. The insufflation system of claim 14 wherein the controller is in communication with the first valve and wherein the controller is configured to regulate the first valve to control a flow rate through the first valve.

16. The insufflation system of claim 14 wherein each of the plurality of flow rate sensors comprises an orifice and a pressure transducer.

17. An insufflation system configured for surgical use with a patient comprising:
    a plurality of flow rate sensors, wherein each of the flow rate sensors is configured to measure flow across a different flow rate range;
    a first valve in fluid communication with the plurality of flow rate sensors and a primary gas delivery line that is connectable to the patient;
    a controller configured to select one of the plurality of flow rate sensors based on a desired flow through the first valve; and
    wherein the first valve is the only valve in the system selectably controllable by the controller to adjust flow rate.

18. The insufflation system of claim 17 wherein each of the plurality of flow rate sensors comprises an orifice and a pressure transducer.

19. The insufflation system of claim 17 wherein each of the plurality of flow rate sensors comprises two pressure transducers.

20. The insufflation system of claim 17 wherein the plurality of flow rate sensors comprise a first flow rate sensor, a second flow rate sensor, and a third flow rate sensor.

21. An insufflation system configured for surgical use with a patient comprising:
    a plurality of flow rate sensors, wherein each of the flow rate sensors is configured to measure flow across a different flow rate range;
    a first valve in fluid communication with the plurality of flow rate sensors and a primary gas delivery line that is connectable to the patient;
    a controller configured to select one of the plurality of flow rate sensors based on a desired flow through the first valve; and
    a delivery manifold configured to distribute gas to the plurality of flow rate sensors and the first valve, wherein flow paths to the plurality of flow rate sensors in the delivery manifold include orifices and are sized based on the flow rate range of the respective flow rate sensors.

22. The insufflation system of claim 21 wherein the controller is in communication with the first valve and wherein the controller is configured to regulate the first valve to control a flow rate through the first valve.

23. The insufflation system of claim 21 wherein each of the different flow rate ranges of the plurality of flow rate sensors only partially overlaps at least one adjacent flow rate range of the different flow rate ranges.

24. An insufflation system configured for surgical use with a patient comprising:
    an insufflator configured to provide gas to the patient during a surgical procedure at gas flow rates ranging from 0.1 liters per minute to at least 50 liters per minute, wherein the insufflator includes a plurality of flow rate sensors, wherein each of the flow rate sensors is configured to measure flow across a different flow rate range;
    a controller in communication with the insufflator, wherein the controller is configured to accept a desired flow rate of gas to be delivered to the patient; and
    wherein the controller is programed to select only one of the plurality of flow rate sensors through which to direct the gas based on the desired flow rate and to control the gas flow rate from the insufflator to the patient to within plus or minus 0.03 liters per minute of the desired flow rate.

* * * * *